United States Patent
Zets et al.

(10) Patent No.: US 11,273,344 B2
(45) Date of Patent: Mar. 15, 2022

(54) MULTIMODAL SENSORY FEEDBACK SYSTEM AND METHOD FOR TREATMENT AND ASSESSMENT OF DISEQUILIBRIUM, BALANCE AND MOTION DISORDERS

(71) Applicant: Engineering Acoustics Incorporated, Casselberry, FL (US)

(72) Inventors: Gary Zets, Maitland, FL (US); Bruce J P Mortimer, Maitland, FL (US)

(73) Assignee: Engineering Acoustics Incorporated, Casselberry, FL (US)

( * ) Notice: Subject to any disclaimer, the term of this patent is extended or adjusted under 35 U.S.C. 154(b) by 394 days.

(21) Appl. No.: 16/384,863

(22) Filed: Apr. 15, 2019

(65) Prior Publication Data

US 2019/0232113 A1     Aug. 1, 2019

Related U.S. Application Data

(63) Continuation-in-part of application No. 13/306,872, filed on Nov. 29, 2011, now Pat. No. 10,258,259, (Continued)

(51) Int. Cl.
    *A61B 5/11*     (2006.01)
    *A61B 5/00*     (2006.01)
    (Continued)

(52) U.S. Cl.
    CPC ............ *A63B 26/003* (2013.01); *A61B 5/112* (2013.01); *A61B 5/1116* (2013.01);
    (Continued)

(58) Field of Classification Search
    CPC . A61B 5/4023; A61B 5/486; A61B 3/00–185; A63B 2022/0094; A63B 2022/0092
    See application file for complete search history.

(56) References Cited

U.S. PATENT DOCUMENTS

| | | |
|---|---|---|
| 5,715,160 A | 2/1998 | Plotke |
| 5,942,954 A | 8/1999 | Galiana et al. |
| | (Continued) | |

OTHER PUBLICATIONS

Non-Final Office Action on U.S. Appl. No. 13/300,428 dated Oct. 31, 2014.

(Continued)

*Primary Examiner* — Devin B Henson
*Assistant Examiner* — H. Q. Nguyen
(74) *Attorney, Agent, or Firm* — Lowndes; Stephen C. Thomas

(57) ABSTRACT

The invention relates to a system and method for measuring the biomechanical state of a subject using various sensors simultaneously with providing the subject with visual exercises for rehabilitation and assessment of disequilibrium, balance and motion disorders. The biomechanical state of a subject is measured during the subject's performance of a predetermined task. Such measurements are useful for the assessment of disequilibrium, balance and motion disorders and are also useful for the determination of therapeutic application of vibrotactile, auditory, or visual feedback to a subject during the subject's attempt to perform a predetermined task. An intelligent controller compares the subject's biomechanical state to a predetermined parameter to determine a variance. If the variance exceeds a threshold, feedback in the form of visual feedback, vibrotactile feedback or auditory feedback may be provided to the subject as a therapeutic means for enabling the subject to compensate for disorder effects.

17 Claims, 12 Drawing Sheets

Related U.S. Application Data which is a continuation-in-part of application No. 13/300,333, filed on Nov. 18, 2011, now Pat. No. 9,526,946, which is a continuation-in-part of application No. 12/201,778, filed on Aug. 29, 2008, now Pat. No. 8,092,355, said application No. 13/306,872 is a continuation-in-part of application No. 13/300,428, filed on Nov. 18, 2011, now Pat. No. 9,149,222, which is a continuation-in-part of application No. 12/201,778, filed on Aug. 29, 2008, now Pat. No. 8,092,355, said application No. 13/306,872 is a continuation-in-part of application No. 12/201,778, filed on Aug. 29, 2008, now Pat. No. 8,092,355.

(60) Provisional application No. 61/415,371, filed on Nov. 19, 2010, provisional application No. 61/418,220, filed on Nov. 30, 2010, provisional application No. 60/966,997, filed on Sep. 1, 2007.

(51) Int. Cl.
*A63B 24/00* (2006.01)
*A63B 26/00* (2006.01)
*A63B 22/00* (2006.01)

(52) U.S. Cl.
CPC .......... *A61B 5/1128* (2013.01); *A61B 5/4023* (2013.01); *A61B 5/486* (2013.01); *A63B 24/0006* (2013.01); *A63B 24/0075* (2013.01); *A63B 2022/0092* (2013.01); *A63B 2022/0094* (2013.01); *A63B 2024/0015* (2013.01); *A63B 2024/0025* (2013.01)

(56) References Cited

U.S. PATENT DOCUMENTS

| | | |
|---|---|---|
| 7,988,287 B1 | 8/2011 | Butler et al. |
| 8,092,355 B2 | 1/2012 | Mortimer et al. |
| 2003/0077556 A1 | 4/2003 | French et al. |
| 2004/0219498 A1 | 11/2004 | Davidson |
| 2006/0058619 A1 | 3/2006 | DeYoe et al. |
| 2006/0217233 A1 | 9/2006 | Lee |
| 2007/0093989 A1 | 4/2007 | Nashner |
| 2007/0121066 A1 | 5/2007 | Nashner |
| 2008/0278682 A1 | 11/2008 | Huxlin et al. |
| 2009/0023122 A1 | 1/2009 | Liberman |
| 2009/0030482 A1 | 1/2009 | Barriskill et al. |
| 2009/0062092 A1 | 3/2009 | Mortimer et al. |
| 2010/0049095 A1 | 2/2010 | Bunn et al. |
| 2010/0322479 A1 | 12/2010 | Cleveland |
| 2011/0152711 A1 | 1/2011 | Della Santina et al. |
| 2013/0241805 A1 | 9/2013 | Gomez |

OTHER PUBLICATIONS

Non-Final Office Action on U.S. Appl. No. 13/300,333 dated Jul. 14, 2014.
Final Office Action issued on U.S. Appl. No. 13/300,333 dated Mar. 3, 2015.
Non-Final Office Action issued on U.S. Appl. No. 13/306,872 dated Mar. 13, 2018.
Non-Final Office Action issued on U.S. Appl. No. 13/306,872 dated Jun. 27, 2016.
Non-Final Office Action issued on U.S. Appl. No. 13/306,872 dated Sep. 19, 2014.

MULTIMODAL SENSORY FEEDBACK SYSTEM AND METHOD FOR TREATMENT AND ASSESSMENT OF DISEQUILIBRIUM, BALANCE AND MOTION DISORDERS

CROSS REFERENCE TO RELATED APPLICATIONS

This application is a continuation in part of U.S. patent application Ser. No. 13/306,872, filed in the United States Patent and Trademark Office (USPTO) on Nov. 29, 2011, titled MULTIMODAL SENSORY FEEDBACK SYSTEM AND METHOD FOR TREATMENT AND ASSESSMENT OF DISEQUILIBRIUM, BALANCE AND MOTION DISORDERS, which shall issue as U.S. Pat. No. 10,258,259 on Apr. 16, 2019, and is hereby incorporated in its entirety by reference; Ser. No. 13/306,872 is a continuation in part of U.S. patent application Ser. No. 13/300,333, titled ENHANCED SYSTEM AND METHOD FOR VIBROTACTILE GUIDED THERAPY, filed in the USPTO on Nov. 18, 2011 and which issued as U.S. Pat. No. 9,526,946 on Dec. 27, 2016, which is hereby incorporated in its entirety by reference; Ser. No. 13/306,872 is a continuation in part of U.S. patent application Ser. No. 12/201,778, titled SYSTEM AND METHOD FOR VIBROTACTILE GUIDED MOTIONAL TRAINING, filed in the USPTO on Aug. 29, 2008, which issued as U.S. Pat. No. 8,092,355 on Jan. 10, 2012 and is hereby incorporated in its entirety by reference; Ser. No. 13/300,333 is a continuation in part of U.S. patent Ser. No. 12/201,778, titled SYSTEM AND METHOD FOR VIBROTACTILE GUIDED MOTIONAL TRAINING, filed in the USPTO on Aug. 29, 2008, which issued as U.S. Pat. No. 8,092,355 on Jan. 10, 2012 and is hereby incorporated in its entirety by reference; Ser. No. 13/300,333 is also a non-provisional of and claims the benefit of provisional patent application Ser. No. 61/415,371, titled ENHANCED SYSTEM AND METHOD FOR VIBROTACTILE GUIDED THERAPY, filed in the USPTO on Nov. 19, 2010, which is hereby incorporated in its entirety by reference; Ser. No. 13/306,872 is also a continuation in part of U.S. patent application Ser. No. 13/300,428 titled ENHANCED SYSTEM AND METHOD FOR ASSESSMENT OF DISEQUILIBRIUM, BALANCE AND MOTION DISORDERS, filed in the USPTO on Nov. 18, 2011 and which issued as U.S. Pat. No. 9,149,222 on Oct. 6, 2015, which is hereby incorporated in its entirety by reference; Ser. No. 13/306,872 is also a non-provisional of and claims the benefit of provisional patent application Ser. No. 61/418,220, titled MULTIMODAL SENSORY FEEDBACK SYSTEM FOR THERAPY AND ASSESSMENTS, filed in the USPTO on Nov. 30, 2010, which is hereby incorporated in its entirety by reference; Ser. No. 13/300,428 is also a continuation in part of U.S. patent application Ser. No. 12/201,778, titled SYSTEM AND METHOD FOR VIBROTACTILE GUIDED MOTIONAL TRAINING, filed in the USPTO on Aug. 29, 2008 and which issued as U.S. Pat. No. 8,092,355 on Jan. 10, 2012, which is hereby incorporated in its entirety by reference; Ser. No. 13/300,428 is also a non-provisional of and claims the benefit of provisional patent application Ser. No. 61/415,371, titled ENHANCED SYSTEM AND METHOD FOR VIBROTACTILE GUIDED THERAPY, filed in the USPTO on Nov. 19, 2010, which is hereby incorporated in its entirety by reference; Ser. No. 12/201,778 is also a non-provisional of and claims the benefit of provisional patent application Ser. No. 60/966,997 titled SYSTEM FOR THE TREATMENT OF BALANCE DISORDERS, filed in the USPTO on Sep. 1, 2007, which is also hereby incorporated in its entirety by reference.

STATEMENT REGARDING FEDERALLY SPONSORED RESEARCH OR DEVELOPMENT

Funded under contract W81XWH-10-C-0155 Treatment of mTBI Balance Dysfunction via Multimodal Biofeedback US SBIR.

INCORPORATION-BY-REFERENCE OF MATERIAL SUBMITTED ON A COMPACT DISK

Not applicable.

BACKGROUND OF THE INVENTION

Field of the Invention

The present invention relates generally to systems and methods for providing multimodal sensory feedback during motional training, and to a system and method for measuring the biomechanical state of a subject while providing them with visual exercises during rehabilitation and assessment of disequilibrium, balance and motion disorders. More specifically, the biomechanical state of a subject is measured during the subject's attempt to perform a predetermined task. Such measurements are useful for the assessment of the presence and severity of disequilibrium, balance and motion disorders. Such measurements are also useful for the determination of the therapeutic application of vibrotactile, auditory, or visual feedback to a subject during the subject's attempt to perform a predetermined task.

Background of the Invention

Balance, or a state of equilibrium, may be described as the ability to maintain the body's position over its base of support. In particular, the optimal posture for controlling balance typically requires maintaining the body's center of gravity (COG) within the base of support, such as the support frames defined by the foot soles. Balance may be divided into static balance and dynamic balance, depending on whether the base of support is stationary or moving. Dynamic balance, even during voluntary movements, is a particularly complex task for humans; stability depends on the kinetics, motor control, sensory information, neuro processing delays and environmental conditions. Ambulation such as exemplified with walking gait, requires anticipatory, reflex and voluntary control of a multi-dimensional biomechanical system, yet is a task that healthy adult humans do with ease.

Disequilibrium and movement and balance disorders can be debilitating and increase the potential for falls. A movement disorder is a condition that prevents normal movement. Some movement disorders are characterized by lack of controlled movement, and while others are characterized by excessive movement. A balance control disorder is typically the result of sensory and/or motor disorders which impair equilibrium control by a subject. Balance control disorders may be bilateral, i.e., affect a subject on both left and right sides, or may only be manifested on one side. Movement and balance disorders may be caused by disorders in the vestibular, somatosensory, or central or peripheral nervous systems.

The vestibular system carries sensory information related to body equilibrium, specifically roll, pitch, and yaw motion oriented relative to the direction of gravity. Information is generated by the semicircular canals and maculae in the inner ear, relayed by the vestibular nerve to the brainstem vestibular nuclei, and processed by the vestibular nuclei and mid brain with corresponding muscular contraction and relaxation known as motor output.

Aspects of the somatosensory system include: 1) perception of pressure, vibration, and texture, i.e., discriminative touch, 2) perception of pain and temperature, and 3) proprioceptive sensation. Proprioception, which is often referred to more generally as the somatosensory system, involves awareness of movement derived from muscular, tendon, and joint articular surfaces provided by the peripheral nervous system and processed in the parietal lobe of the brain. These interoception senses provide internal feedback on the status of the body, indicating whether the body is moving with required effort and indicating where various parts of the body are located in relation to each other. Thus, proprioception involves the essential stimuli provided to, or received by, skin, joints, and/or muscles to maintain equilibrium or balance control.

Damage to any part of the central or peripheral nervous systems may interfere with balance control. Central nervous system processing includes the brain primary motor cortex responsible for generating the neural network impulses controlling execution of movement, the posterior parietal cortex responsible for transforming visual information into motor commands, the premotor cortex responsible for sensory guidance of movement and control of proximal and trunk muscles of the body, and the supplementary motor area responsible for planning and coordination of complex movements such as coordinated activity using limbs.

In particular, vision plays a significant role in balance. Indeed, up to twenty percent of the nerve fibers from the eyes interact with the vestibular system. A variety of visual dysfunctions can cause disequilibrium. These dysfunctions may be caused directly by problems in the eyes, or may be caused indirectly by disorders related to stroke, head injury, vestibular dysfunction, deconditioning, decompensation, or the like.

Meanwhile, the peripheral nervous system generally relates to the conduction of sensory information, or messages, from the peripheral nerves to the brain and spinal cord. For example, such sensory information may indicate that there is a pressure on the sole of a foot or that a toe is flexed. Sensory information may also indicate that the feet are cold or that a finger is burned.

Accordingly, the body relies on the interaction of several systems to control movement, balance, and posture. For example, the vestibular system in the ears orient upright stance, especially when the eyes are closed. The cutaneous, proprioceptive sensory system feels pressure under the feet. In addition, the joint and muscle spindles are sensitive to joint position and movement. Moreover, cognition or brain processing estimates the motor response magnitude. In sum, balance disorders are predominantly multi-causal with imbalance occurring due to deficits in more than one sensory, motor, neuro or cortical pathway.

Traumatic brain injury (TBI) or mild traumatic brain injury (mTBI), occurs when physical trauma causes temporary or permanent neurological damage. mTBI typically involves temporary impairment of neurological function which usually quickly resolves by itself, and conventional neuroimaging normally shows no gross structural changes to the brain as the result of the condition. Overt symptoms may often include balance (M. Scherer and M Schubert, Traumatic Brain Injury and Vestibular Pathology as a Comorbidity After Blast Exposure, PHYS THER. Vol. 89, No. 9, September 2009, pp. 980-992) and spatial disorientation problems (vertigo) related to vestibular dysfunction, vision disturbances, inner-ear edema, and/or other sensory integration deficits.

Recently, it has been found that blast related injury patterns are different compared to those caused by impact (M Hoffer, K Gottshall, B Balough, C Balaban, Vestibular Difference Between Blast and Blunt Head Trauma, ARO, Abstract 50, Feb. 20, 2008). Overt symptoms may include balance and spatial disorientation problems (vertigo) related to vestibular dysfunction, vision disturbances, inner-ear edema, and/or other sensory integration deficits. Treatment of this particular population group has several challenges that for the military include; early and specific injury assessment, the determination of appropriate return-to-duty for subjects and effective balance rehabilitation treatment tools. The group is also highly variable in the nature and extent of balance deficit, although it appears that almost all subjects show susceptibility to ocular motion disorders.

The vestibular-ocular reflex (VOR) integrates eye movements with head motion and therefore assists with dynamic balance. Other automated accommodation eye movements include vergence, which involves simultaneous movement of both eyes in opposite directions to obtain or maintain single binocular vision, and smooth pursuit movements, which track slow moving visual targets. The visual system in healthy individuals is well adapted to maintaining focus during typical postural movements. This is due to the vestibular system measuring any resultant linear and angular head movements and accelerations, and via the VOR automatically compensating for said movements, thereby maintaining visual control. Therefore any vestibular dysfunction can be extremely debilitating, as even simple visual tasks cannot be accomplished and in most cases, subjects complain of visual blurring and motion sickness.

The assessment and treatment solution for mTBI disorders is currently through a multidisciplinary team. Assessment of postural control may be partially through the measurement of muscle response using techniques such as electromyography (EMG), kinematic analysis of body movement using video, optical tracking, ground reaction forces and body worn sensors. However, postural control is the result of an integration of multiple sensory systems, multiple degrees of freedom and passive and dynamic aspects. Therefore assessment must often identify causal factors amongst cross coupled systems. Computerized dynamic posturography (see for example Nashner L M, McCollum G (1985) The organization of human postural movements: a formal basis and experimental synthesis. Behav Brain Sci 8:135-172 and Nashner L M, Black F O, Wall C (1982) Adaptation to altered support and visual conditions during stance: subjects with vestibular deficits. Journal of Neuroscience 2:536-544) has been suggested as a method for analyzing postural responses during the maintenance of stance. Sensory information can be restricted or made inaccurate resulting in decreased performance—comparing normal, age group groups to a subject response gives a potential indication and identification of sensory deficits. Although this approach has some clinical use, it does not easily address deficiencies in the vestibular system that may be highly position and acceleration dependent, nor do prior art approaches address therapy.

Therefore there is a clear need for objective measurements both to assess the subject's original vestibular ocular or related neurological deficit, and their rate of progress through rehabilitation. Data capture and analysis, even while completing therapeutic activities (for example during functional movement tasks) can be used to provide quantitative information to the therapist, optimize motional limit tasks and adaptively alter feedback settings and motional task difficulty. In particular, certain functional dynamic visual acuity tasks are known in prior art to be reliable and accurate indicators of behavior functional ability. However, previous efforts to measure performance during functional gait tasks often rely on human observations and subjective scoring and are difficult to interpret.

After assessment of disequilibrium, rehabilitation is often a course of remedial physiotherapy, administered by a physiotherapist (PT), physiotherapy assistant (PTA), and other professionals, more generally referred to hereinafter as the therapist. There is a very limited pool of specialist PT's who specialize in the treatment of neurological problems resulting from brain or spinal cord injuries. Individual treatment programs (e.g., vestibular rehabilitation) are designed by these specialist PT's who also monitor and participate in each subject's recovery. Thus rehabilitation is extremely labor intensive and time consuming. Treatment options for subjects with dizziness and balance problems due to vestibular damage, are typically therapist administered habituation exercises that require the subject to move their head, while attempting to keep their eyes focused on targets.

Habituation exercises, first described by Cawthorne and Cooksey in the 1940s (see Cawthorne, T: The Physiological Basis for Head Exercises. The Journal of The Chartered Society of Physiotherapy 30:106, 1944., Cawthorne T. Vestibular injuries. Proc R Soc Med 1946;39:270-272. And Cooksey F S. Rehabilitation in vestibular injuries. Proc R Soc Med 1946;39:273-275), consist of a series of eye, head, and body movements that provoke vestibular symptoms, which theoretically fatigue the vestibular response and force the CNS to compensate by habituation to the stimulus. Habituation exercises are used for subjects experiencing from motion or position-provoked symptoms. Recovery from a peripheral vestibular lesion results from a combination of the restoration of peripheral labyrinthine function and central vestibular compensation. The goal of vestibular exercises is to accelerate the process of vestibular compensation and improve the final level of recovery. Indeed, controlled studies in animals and humans indicate that exercising can accelerate the recovery of balance after a peripheral vestibular lesion, indicating the importance of properly administered compensation and habituation exercises.

Typical compensation and habituation exercises typically focus on adaptation of the vestibular-ocular reflex (VOR) and may consist of various functional activities where the subject is asked by the therapist, to perform head movements while keeping a target in focus. For example, the therapist may present a visual target (such as a card with a word written on it) into the field of view of the subject, the subject may then be asked to look at a target while simultaneously moving their head side to side, at a head rotation rate and extent where the target is kept in focus. For effective therapy, the subject should perform the exercise at frequencies that result in subtle nausea, and perform this for several minutes. It should be noted that prior art habituation exercises rely on the subject's compliance with a complex and dynamic task. In particular, the habituation exercises should optimally be progressed in difficulty during the therapy session, requiring the subject (under the direction of the therapist) to gradually increase head movement rate to a level just slower than when the target falls off focus.

With any VOR exercise, the adaptation is very specific, and the exercise should be preferably performed at different speeds and with diverse configurations so that the adaption may be effectively transferred to general functional movements. These functional VOR exercises rely on the direction of a specialist therapist, and the subject complying with the instructions. This process is very time consuming, error prone and inefficient especially as the therapist is usually unaware of where the subject is actually looking.

It is therefore an object of the present invention to provide multimodal sensory feedback during motional training. Further a system and method for providing a subject with effective visual vestibular ocular exercises during balance rehabilitation and assessment.

SUMMARY OF THE INVENTION

The present invention relates generally to systems and methods for providing multimodal sensory feedback during motional training, and, more particularly, to a system and method for providing a subject with visual exercises during balance rehabilitation and assessment.

DETAILED DESCRIPTION

Figure 1:
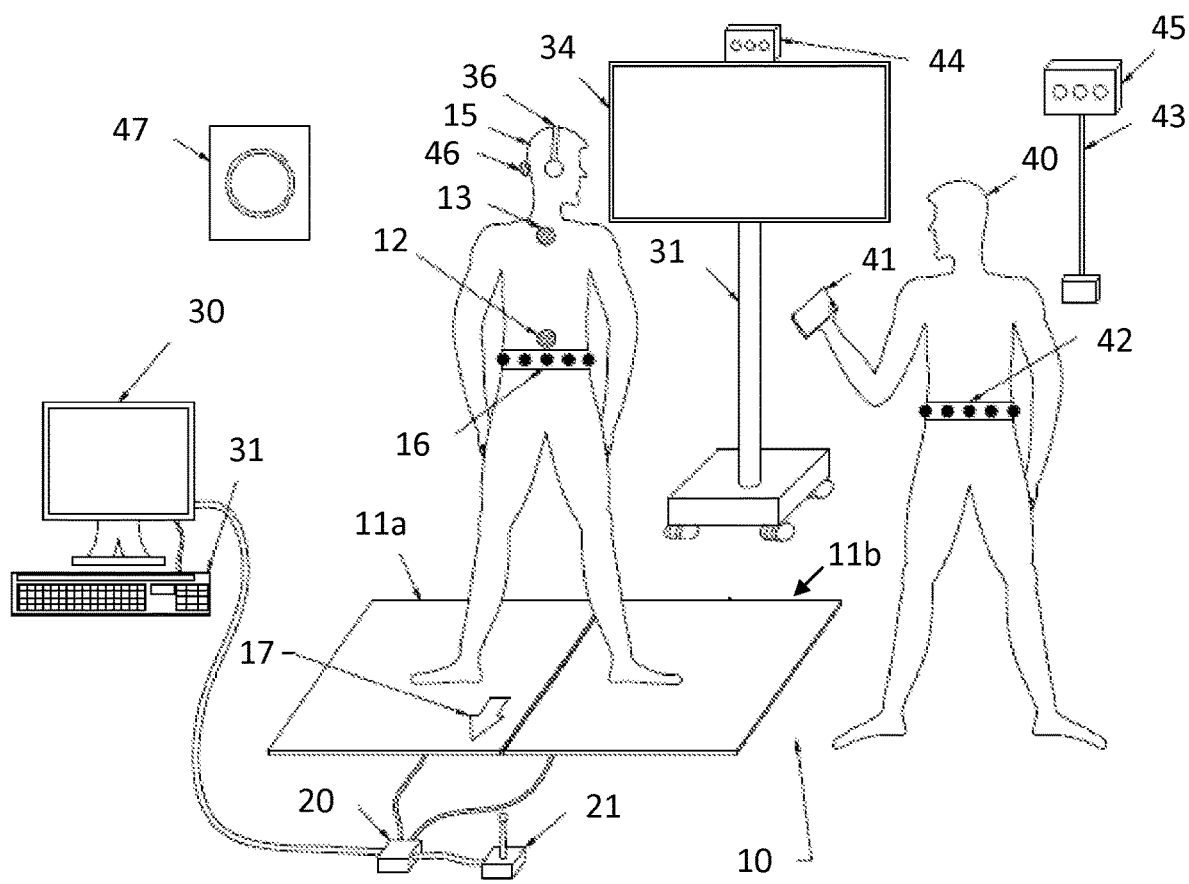
FIG. 1 illustrates an embodiment of a multimodal sensory feedback motional training system according to aspects of the present invention.

The following documentation provides a detailed description of the invention.

Although a detailed description as provided in the attachments contains many specifics for the purposes of illustration, anyone of ordinary skill in the art will appreciate that many variations and alterations to the following details are within the scope of the invention. Accordingly, the following preferred embodiments of the invention are set forth without any loss of generality to, and without imposing limitations upon, the claimed invention. Thus the scope of the invention should be determined by the appended claims and their legal equivalents, and not merely by the preferred examples or embodiments given.

Embodiments according to aspects of the present invention provide systems and methods for providing a subject with assessment or motional training, or both. In particular, embodiments provide motional training by providing a subject with combinations of multimodal sensory feedback that include, visual, auditory and vibrotactile feedback, in response to an attempt by the subject to perform predetermined motions.

The embodiments provide spatial orientation and/or timing feedback cues via multisensory mechanisms to guide postural and mobility decisions. Real time combinations of vibrotactile, auditory and visual displays may therefore be provided as multisensory feedback to cue appropriate motions by the subject. In addition, such feedback may also be used to correct abnormal movement that can occur during functional tasks. Unlike the prior art, the embodiments recognize that sensory feedback requirements are context sensitive, and thus employ multisensory stimulation that may vary by type, location, duration, etc. to provide information that relates closely to each stage of the functional activity. Thus, in some embodiments, the multisensory feedback is provided according to specific, and often well-understood, sub-tasks, thereby restricting the context and simplifying the control intelligence.

For example, the approaches to motional training described herein may be employed to treat balance disorders. Subjects with balance disorders may be trained to perform basic functional tasks and sub-tasks, so that the subjects learn balance strategies and retain the skills needed to prevent falls. In general, aspects of the present invention take advantage of the brain's ability to re-organize and re-learn the functional tasks and sub-tasks. Thus, embodiments provide a tool by which a subject and a therapist may determine the limits of stability and understand how the subject can learn/relearn functional tasks and sub-tasks.

In another example, the approaches to motional training described herein may be employed to treat and assess vestibular ocular disorders. Subjects with vestibular ocular disorders may be trained to perform basic vestibular ocular functional tasks and sub-tasks, so that the subjects learn compensation strategies, regain dynamic visual acuity and retain the skills needed to prevent falls. Thus, embodiments provide a tool by which a subject and a therapist may determine vestibular ocular system performance, and provide a system and method whereby the subject can learn/relearn vestibular ocular functional tasks and sub-tasks, and more specifically improve vestibular ocular gain performance.

In addition, embodiments allow such tasks to be scripted from a set of defined sub-tasks tailored to a subject. In other words, embodiments provide for the design of new tasks or the concatenation of different sub-tasks together to define more complex tasks. Of particular interest are functional activities that involve graduated transitional motion, i.e., changing the task difficulty according to the needs and ability of the subject. For example, various vestibular ocular functional therapeutic and assessment tasks, may require several different visual, head movement, and visual target related tasks and sub-tasks. In some instances, static or moving visual scenes or backgrounds may be included to add visual distraction which further increase task difficulty.

The sequence from one stage to the next may require well bounded temporal (timing) and spatial (kinematical) conditions to be achieved, and compliance on the part of the subject. Compliance with the task is also an indication of the subject's capability. Therefore the task should preferably be graduated in difficulty, such that the subject exercises mostly within their current capability. Further, the subject's capability can be measured by determining the subject's performance during several tasks with various difficulty levels.

Moreover, because the object of clinical treatment is the transfer of knowledge and experience to the subject during the treatment, embodiments facilitate dynamic modifications to accommodate the special needs of each subject and to adapt dynamically to challenge the subject to achieve new skill levels when the subject has mastered a certain task. This dynamic process is believed to be related to brain plasticity. Thus functional activities, after a training and evaluation period, may be repetitively practiced in a clinical setting using an environment that adaptively changes task difficulty as well as the number of tasks. Some embodiments also contemplate a take-home system that is programmed with the characteristics and requirements tailored to specific subjects, at a specific stage in their training or treatment, allowing subjects to continue motional training therapy in the home environment.

Vestibular rehabilitation for subjects balance dysfunction particularly target the vestibular-ocular reflex, cervico-ocular reflex, depth perception and somatosensory retraining. Therefore, prescribed functional exercises may typically focus on adaptation of the vestibular-ocular reflex (VOR) and may consist of the subject performing head movements whilst simultaneously keeping a target in visual focus. The subject should preferably perform the exercise at frequencies that result in subtle nausea, and perform this for an extended period. It is known in the art that rehabilitation exercise repetition may lead to habituation and compensation due to internal recovery mechanisms such as brain plasticity and the development of alternate mechanisms that compensate for the original injury or vestibular deficit. It is also known, that the rehabilitation exercises should preferably be progressive in difficulty; by pushing the subject's head movement rate to a level just slower than when the target falls off visual focus. Further, it is known that rehabilitation exercises should preferably be diverse; for example, adaptation of the VOR can be complicated by moving the target in the opposite direction of the head movement. Therefore, preferable rehabilitation exercises may also include activities such as arm and head movements that are intentionally in opposite directions, thereby forcing a doubling of the VOR gain needed for the eyes to stay on target.

Another vestibular rehabilitation method known in the art, associated with coordinating a subject's eye and head movements, may use two targets that are placed approximately 3-4 feet apart on a wall in front of the subject. The subject looks and aligns their head with a first target, and then without moving their head, initially looks at a second target first with only their eyes, and subsequently moves their head to be in alignment with the second target. The sequence is repeated and the subject's eyes should not drift off the target. As with any VOR exercise, the adaptation is very specific, and the exercise should be performed at different speeds and in the vertical plane as well as the horizontal plane. Once various speeds are accomplished, the exercises can be further maximized by performing them with a complex background (see for example Susan Herdman, Vestibular Rehabilitation, Contemporary Perspectives in Rehabilitation, 2007 incorporated herein by reference).

However, these prior art functional VOR exercises rely on the subject complying with the instructions. Further, the therapist is usually unaware of where the subject is actually looking. Changes in VOG are also prone to error especially in cases where a subject's postural control is poor; these typically result in large sways and head movement perturbations which will require vestibular ocular reflex corrections or result in perceived visual target blurring or oscillopsia. Embodiments according to aspects of this invention, provide a system and method for the computerized assessment of a subject's vestibular ocular system functional performance, and provide a system and method for graduated motional training functional activities that promote adaptation and habituation of the subject's vestibular ocular system, based on the measured abilities and compliance of the subject during said activities.

Recent studies have also demonstrated the importance of coordinating the motions of the head and trunk during the maintenance of balance. The addition of active head movements to a postural task will result in degradation of postural control performance (see for example Paloski, W. H., Wood, S. J., Feiveson, A. H., Black, F. O., Hwang, E. Y., and Reschke M. F. Destabilization of human balance control by static and dynamic head tilts. Gait & Posture 23(3): 315-323, 2006, incorporated herein by reference). In other words, head movements significantly increase the difficulty associated with a static (for example steady stand) or dynamic (for example gait) balance task and, head movements are important to include as components of functional tasks within motional training activities.

Head movements in particular provide simultaneous stimulation of the peripheral vestibular system while performing a postural control task and the brain must discriminate body sway and head movement stimuli in order to maintain adequate balance. Further, subjects with balance system disorders commonly complain that moving the head and eyes while maintaining standing balance frequently provokes symptoms of dizziness and unsteadiness. As described hereinbefore, rehabilitation is usually through a series of exercises that are aimed at adaptation and compensation of the vestibular ocular system. The process of compensation depends on various mechanisms, including substitution strategies, prediction strategies, and cognitive strategies. It is an object of this invention to provide a system and methods for providing graduated transitional motion, and visual feedback configurations for vestibular ocular system recovery. Specifically, inventive features include; measuring a subjects vestibular ocular task capability, providing methods for triggering the abnormal VOG symptoms in order to "desensitize" the vestibular system (habituation) for positional or motion-provoked symptoms, providing methods for adapting to improve the gain of the vestibular ocular reflexes, and providing methods for substituting alternative senses to replace lost vestibular function by biasing use away from the dysfunctional vestibular input.

When vestibular rehabilitation therapy is combined with multimodal feedback, as described in this invention, this results in an augmentation of the information available to the subject for sensory integration and enhanced postural and spatial awareness. In general, therapist administered balance therapy is both problem and task orientated; problems that are identified during evaluation are treated by tailoring a specific program for the subject, and are further adapted or modified during the course of therapy (Susan Herdman, Vestibular Rehabilitation $3^{rd}$ Ed, Chapter 20—Interventions for the subject with vestibular hypofunction, Contemporary Perspectives in Rehabilitation, 2007). Therefore the therapist is well accustomed to using functional activities during therapy, altering the parameters associated with the functional activities (for example the speed of exercises, changing activity position, changing the environmental conditions and context and exposing the subject to concurrent multiple tasks). However, this is done in an uncontrolled manner and therefore the effectiveness of therapy often relies on the skills of the therapist. Although there are many standard functional tasks, the order and task configuration is usually determined by the therapist. Therapists are also able to innovatively combine activities and introduce therapeutic tasks using very low tech (and low cost) additions such as foam for disrupting somatosensory information, or using visual-conflict domes for disrupting vision (Anne Shumway-Cook and Marjorie Woollacott, Motor Control, Chapter 11, Clinical Management of the Subject with a Postural Control Disorder, $2^{nd}$ Ed, Lippincott Williams and Wilkins, 2001).

The components associated with general balance retraining typically include static and dynamic functional balance exercises with transitions between different sensory conditions, more generally defined as motional training. It is an object of one embodiment of this invention, to provide motional training by providing a subject with combinations of multimodal sensory feedback that include, visual, auditory and vibrotactile feedback, in response to an attempt by the subject to perform predetermined motions. Motional training tasks will typically include predetermined activities such as steady stand, stand and twist, reach, and dynamic activities such as gait, stepping, sit to stand and turns. Motional training tasks may also be modulated by changing the base of support of the subject, for example by altering the support surfaces, such as a rocker board, foam, or narrow beam, standing in a tandem position, a semi-tandem position, on one leg, or in a feet together position. Tasks may also be progressed by adding simultaneous alterations of visual and vestibular inputs as will be described in more detail hereinafter. Similarly, the sensory cues available to the subject may be altered by instructing the subject to close their eyes, or to engage vision with a secondary task.

Referring now to FIG. 1, a multimodal sensory feedback and motional training and assessment system 10 according to aspects of the present invention is illustrated. The multimodal sensory feedback motional training system 10 may be operated by a therapist 40 to provide motional training for a subject 15. In general, the motional training and assessment system 10 comprises of various combinations of sensors that measure the biomechanical state and characteristics of a subject 15, provides biological state measurements to an intelligent controller 20 and during predefined motional training activities, provides the subject 15 multimodal feedback in combination with said activities. Multimodal sensory feedback comprises combinations of auditory, visual and vibrotactile feedback as described in detail hereinafter. Biomedical state is the positional, mechanical and kinematic data associated with the subject at a particular time or time period, and include features such as center of pressure (COP), center of Gravity (COG), trunk angle, postural characteristics such as subject's orientation (direction the subject is facing), position (such as sitting, standing, leaning, bending), and postural variables such as head orientation, eye gaze direction, limb position, limb COG, ankle and hip position, as well as velocity and acceleration associated with these variables. Biomedical state measurements are the values or data provided by the one or more sensors that are used to measure biological states.

In an example application, the multimodal sensory feedback motional training system 10 may be employed to treat balance disorders in the subject 15. As shown in FIG. 1, the subject 15 is situated on force plates 11a and 11b, while a vibrotactile feedback mechanism 16 as well as optional inertial sensors 12, and 13 are mounted on, or coupled to, the subject 15. Meanwhile, another vibrotactile feedback mechanism 42 may be mounted on the therapist 40. A visual feedback display 34 is provided, optionally mounted on a movable stand 35 together with a means for providing auditory feedback, such as headphones 36 or one or more loudspeakers 47, positioned at various spatial locations surrounding the subject 15. A second optional visual display monitor 30 may also be provided with a keyboard interface 31, and both may be connected to the intelligent controller 20 to provide a user interface. Alternately, the functions of the user interface may be provided by the visual feedback display 44. The therapist 40 may also operate aspects of the multimodal sensory feedback motional training system 10 via a remote interface 41 as shown in FIG. 1. A light weight inertial sensor 46 is worn on the head of the subject 15. The head worn inertial sensor 46 can also be integrated into the headphones 36. Preferably body worn sensors and actuators should use wireless 21 connectivity to the intelligent controller 20. In general, the multimodal sensory feedback motional training system 10 may be operated with an intelligent controller 20, which may be any processing device, such as a conventional desktop computer, that can execute programmed instructions (or system software) provided on media well known in the art, such as computer-readable memory. In certain embodiments of the invention, the subject 15 may operate aspects of the system 10 individually.

The force plates 11a and 11b, the vibrotactile feedback mechanism 16, the visual feedback display 44, the auditory feedback headphones 36 or loudspeakers 47, and the inertial sensors 12, 13 and 46 may communicate with the intelligent controller 20 via conventional wired or wireless connections. For example, the force plates 11a and 11b may communicate directly to the intelligent controller 20 using a wired connection, such as a conventional universal serial bus (USB) connection or the like. Meanwhile, a wireless data connection 21, such as Bluetooth or the like, shown in FIG. 1 may allow the intelligent controller 20 to communicate with the vibrotactile feedback mechanism 16, wireless headphones 36 or loudspeakers 47, wireless visual feedback display 44, and the inertial sensors 12, 13 and 46. In addition, the remote interface device 41 may also use a wireless interface to connect to other components of the multimodal sensory feedback motional training system 10. In general, wireless communications may be particularly suitable for components of the multimodal sensory feedback motional training system 10 that must move easily with the subject 15 or the therapist 40; however, it is not required that these connections are wireless. The form of electrical communication between the components of the system of the invention may take any form well known in the art such as wired, wireless optical, or any other form and is not to be construed as a limitation of the scope of the claims herein In other embodiments, the components (visual display monitor 30, intelligent controller 20, keyboard interface 31 and wireless data connection 21) may be integrated within one composite unit, for example a touch-screen all-in-one computer.

The force plates 11a and 11b provide a technique for measuring body sway in terms of displacement of the center of foot pressure (COP), generated by the inherent instability of the subject 15 standing on the fixed support surface of the force plates 11a and 11b. The COP is computed from the signals provided by force transducers which are typically embedded in the corners the force plates 11a and 11b. The force transducer outputs are processed to obtain a projection of the resultant forces acting at the subject's center of gravity (COG) via the force plates 11a and 11b.

In general, a force plate is a sensor that measures the load at discrete points mounted beneath a relatively rigid plate. The load is usually measured using load-cell type sensors, converted into an electronic voltage signal and sampled using an analog to digital converter to be in a form suitable for computer or microcontroller processing. The response from one or multiple force plates can be combined using known analog to digital and mathematical algorithms implemented in computer software. The load cells and measurement conversion electronics in the embodiment of FIG. 1 may be configured to be accurate for a range of subject weights, for example from approximately 100 to approximately 300 pounds.

Although the embodiment of FIG. 1 illustrates two force plates 11a and 11b positioned adjacent to each other to form a combined area, any number and/or configuration of force plates may be employed to produce an active area that is sufficiently large to support the subject 15 while standing and/or performing predetermined motions as described further below. For example, the combined area of the force plates 11a and 11b may be greater than approximately 20 inches by approximately 11 inches.

Although the sensors used in some embodiments may be limited to the use of force plates 11a and 11b, the embodiment of FIG. 1 also employs the optional inertial sensors 12, 13 and 46. As illustrated in FIG. 1, the inertial sensor 12 may be mounted proximate to the center of gravity (COG) of the subject 15, i.e., in the area of the lower back of the subject 15. The inertial sensor 12 may be mounted according to any suitable arrangement. For example, the inertial sensor 12 may be incorporated with a belt or garment worn by the subject 15. Alternatively, the inertial sensor 12 may be incorporated into the vibrotactile feedback mechanism 16 worn by the subject 15. Meanwhile, the inertial sensor 13 may be mounted higher on the upper body of the subject 12, for example at the back of the neck proximate to the top of the spine. The inertial sensor 13 may be incorporated in a garment or accessory worn by the subject 15. Accordingly, the inertial sensor 12 provides information regarding the orientation and motion of the COG, while the inertial sensor 13 second sensor provides information regarding the orientation and motion of the upper body of the subject 15, and inertial sensor 46 provides information regarding the orientation and motion of the head of the subject 15.

Commercially available inertial sensors are typically provided with on-board intelligent processing, real-time signal filtering, and digital interfacing. In particular, each inertial sensor 12, 13 or 46 may be a three-axis device that employs accelerometers and magnetometers. In some embodiments, the three-axis device may combine three-axis accelerometers with a magnetometer to provide a tilt sensor. In other embodiments, the three-axis device may employ gyroscopes to provide higher resolution than the tilt sensors, which are angular rate limited due to filtering and may be prone to drift.

The choice of sensor is typically based on resolution and costs constraints. For example, the measurement of spine angle during a sit to stand transition will require less resolution in clinical systems where the primary body orientation is measured using a force plate sensor. In this example, an accelerometer or low cost inertial device will provide sufficient accuracy for this task. However, for a stand-alone inertial sensor, a precision sensor (i.e. one that includes three axis accelerometers, gyroscopes and magnetometers) is preferably used.

There are some advantages in using multiple inertial sensors, particularly one mounted at the base of the spine and one just above the shoulder blades as shown in FIG. 1. Multiple sensors that are interconnected can be used to null some common mode errors and can be used to more accurately calculate the relative dynamic motion of the body trunk located between the sensors.

There are advantages to combining inertial sensors (or multiple inertial sensors) with a force plate as shown in FIG. 1, because a more accurate measurement of COG can be performed. Balance and specifically the limits of balance during dynamic activities (and especially large postural changes) will result in a significant mismatch between COG and COP. Trunk and or limb dynamic movement can be directly measured with an inertial sensor and used together with force plate data to obtain an accurate estimation of body orientation and dynamic motion.

In other embodiments of the multimodal sensory feedback motional training system 10, one or more three dimensional (3D) camera sensors 44 and 45 may be individually, or in combination with other sensors, used to obtain information regarding the orientation of the subject 15 while standing or performing predetermined motions as described further below. Various methods are known in the art for optical 3D mapping, i.e., generating a 3D profile of the surface of an object by processing an optical image of the object. Some methods are based on projecting a speckle pattern onto the object, and then analyzing an image of the pattern on the object (for example U.S. Pat. No. 7,433,024). These systems reconstruct a 3D map of the object or subject. The term "3D map" refers to a set of 3D coordinates representing the surface of a given object, in this case the user's body. In other designs, the 3D camera device projects a pattern of spots onto the object and captures an image of the projected pattern, and then computes the 3D coordinates of points on the surface of the user's body by triangulation, based on transverse shifts of the spots in the pattern. Methods and devices for this sort of triangulation-based 3D mapping using a projected pattern are described, for example, in PCT International Publications WO 2007/043036, WO 2007/105205 and WO 2008/120217, whose disclosures are incorporated herein by reference. Alternatively, 3D cameras may use other methods of 3D mapping, using single or multiple cameras or other types of sensors, as are known in the art. By way of example, the Microsoft Kinect exemplary system provides a low cost 3D camera sensor.

The 3D camera sensor 44, the vibrotactile feedback mechanism 16, auditory feedback headphones 36 or loudspeakers 47, and the optional inertial sensors 12, 13 and 46 may communicate with the intelligent controller 20 via conventional wired or wireless connections. For example, 3D camera sensor 44 may communicate directly to the intelligent controller 20 using a wired connection, such as a conventional universal serial bus (USB) connection or the like.

The 3D camera sensor (44 or 45) provides an instrument for measuring body sway as well as the biomechanical features such as, joint positions and angles of the subject 15 who is standing within the field of view of one or more 3D camera sensors. Specifically the 3D camera sensor provides a 3D map or image field to the intelligent controller. Image processing software on the intelligent controller processes the data, identifying the subject 15 in the image data field, identifying body segments (such as the torso or limbs) and tracking their position and orientations. Each segment can have combinations of translational and rotational degrees of freedom (DOFs) relative to a parent segment. The system automatically constructs the geometric postural skeleton structure, DOF relations, and DOF constraints between segments according to biomechanical principles that are well known in prior art. Each segment can be weighted and used in a skeletal model to calculate the body center of gravity (COG) location (as for example, described in V. Zatsiorsky "Kinetics of Human Motion" Section 4.3, Human Kinetics, 2002). Further, it may also be advantageous to calculate anterior-posterior (AP) (forward-backward) and medio-lateral (ML) (side-to-side) components of the COG and trunk sway angles from the postural segment data and display this in real time on a visual display. The center of gravity (COG) and trunk sway data for the subject can be readily calculated, in real time, by the intelligent controller. The data processing rate is usually restricted by the framing rate of the 3D camera sensor (for example 30 frames per second) however this is fast enough for real time motional therapy analysis.

Similarly, biomechanical features such as the trunk angle and position can be measured and the dynamic movement strategies of the subject can be estimated by the intelligent controller 20. For example, it is well known in prior art that static stance movement strategies may use ankle torque (or ankle strategy) or hip flexure (hip strategy) or a combination of the two during balance. Therefore, if the body segments are known at each frame instant (and the feet positions are fixed), the balance strategy can be identified from the trunk sway angle and relative angles between the ankle to hip (lower body segment) segment and hip to upper body (trunk) angle. If the upper and lower body segments move in the same direction or in phase with one another, then ankle strategy is being used and the human stance can be modeled as an inverted pendulum. Since the amount of force that can be generated by the muscles surrounding the ankle joint is relatively small, this strategy is generally used to control standing sway through a very small range of motion. In contrast to the ankle strategy, the hip strategy involves activation of the larger hip muscles and is used when the center of gravity must be moved more quickly back over the base of support as the speed or distance of sway increases. When using the hip strategy, the upper body (trunk) moves in a direction opposite to that of the lower body. Subjects may interchange between these postural control strategies (for example after instruction, environment). However, if the center of gravity is displaced beyond a maximum limit, or the speed of sway is so fast that the hip strategy is insufficient to maintain stability, then stability can only be maintained by finding a new base of support, for example by stepping. The 3D camera sensor 44 is advantageous as the complete motion and postural strategy employed by the subject 15 can be automatically determined by the intelligent controller 20, and displayed to the therapist 40.

Further, in other embodiments of this invention, one or more 3D camera sensors (44, 45) can be used to track and measure the subject's 15 head angle and position. As described in further detail hereinafter, the direction of gaze and orientation of the head with respect to a visual display 34 can be estimated by the intelligent controller 20, and used during motional training activities that address habituation of vestibular ocular system and related neurological systems.

Therefore one or more 3D camera sensor 44 and 45 are advantageous as the complete motion and postural strategy employed by the subject 15 can be determined by the intelligent controller 20 and displayed on the screen 34 or therapist 40 remote interface 41.

3D camera sensor 44 (and 45) will result in a sensor field of view with a defined vertical, horizontal and depth range (this will be determined by the height of the sensor, the design and environment). Typical 3D camera sensors may have reasonable horizontal and vertical accuracy, but will have less precision in depth. Further, areas that are located behind opaque objects in the field of view of the sensor cannot be resolved. Therefore it is beneficial to use two or more 3D camera sensors 44 and for example 45, that are located with different, intersecting fields of view, to provide a more accurate and robust calculation of the biomechanical joint positions and angles of the subject 15 who is standing within the field of view of the sensor. For example, 3D camera sensor 44 may be placed on a wheeled stand 35, with another 3D camera sensor 45 located distal to the first, thereby orientating the sensors with different aspects and orientations to the subject.

In other embodiments, multiple 3D camera sensors 44, 45 can be used to increase the operation range or measurement capabilities of the motional training system 10. For example, 3D camera sensors 45 can be located on stand 43, to be off axis, but predominantly facing the subject 15. Multiple 3D camera sensors 44 and 45 should preferably be located orthogonally, approximately 2 m from the subject 15, thereby utilizing the full usable measurement range of the sensors and providing an accurate measurement of the anterior-posterior (front backwards) as well as medio-lateral (side to side) movement of the subject 15.

The subject 15 orientation and example movement with respect to each of the sensors can be detected and classified by the intelligent controller 20. Thereby a method for extracting the most accurate features from each sensor (for example placing greater priority on measurements that are not depth related) may be used by the intelligent controller. The measurements of the subject 15 biomechanical features (such as COG, joint angles and positions) are therefore combined from multiple sensors (mapping, scaling and weighting as necessary) into a more precise composite system based measurement.

In general, the motional training system includes one or more sensors that measure appropriate subject body orientation and approximate the location of the center of gravity (COG). In certain cases, is possible to select other biomechanical features from the sensor information. For example, subject 15 trunk sway angle may be readily used in place of COG provided that the degrees of freedom for the biomechanical system are limited (as would be the case for upright stance without hip flexure). In other examples, head orientation and position may be measured and used in motional training activities and assessments related to the habituation of the vestibular ocular system. As described in detail below, sensor information is used together with knowledge of various functional activities to predict and compare the actual body response and posture during various stages of each particular functional movement therapy or assessment task.

The choice and combination of sensors is based on the resolution and cost constraints. A lightweight force plate is low cost, robust and able to provide center of pressure (COP) positional and ground reaction force information (as described hereinbefore). Multiple force plates can be attached together in various embodiments in order to construct a wide sensing area. There are also advantages to combining inertial sensors (or multiple inertial sensors) with a force plate as shown in FIG. 1, because a more accurate measurement of the subject 15 biomechanical state and postural characteristics can be performed. For example, during certain dynamic activities (and especially large postural changes) there may be a significant mismatch between COG and COP. Trunk and or limb dynamic movement can be directly measured with an inertial sensor and used together with force plate data to obtain an accurate estimation of body orientation and the actual dynamic motion. During dynamic activities, force plate data can be supplemented with multiple measurements of body segment COG and processed by the intelligent controller 20 to determine a more representative biomechanical state of the subject 15. There are some advantages in combining multiple inertial sensors, particularly one mounted at the base of the spine and one just above the shoulder blades as shown in FIG. 1. Multiple sensors that are interconnected can also be used to null some common mode errors and can be used to more accurately calculate the relative dynamic motion of the body trunk located between the sensors.

Similarly, the 3D camera sensor (for example 44) provides an instrument for measuring the position, body sway as well as the biomechanical joint positions and angles of the subject 15 who is standing within the field of view of the sensor, without the need to couple the sensor to the subject. Specifically the body segments (such as the torso or limbs) are identified from the 3D camera sensor image field (sensor output) and their position and orientations can be individually tracked by the intelligent controller 20. Therefore the center of gravity (COG) for the subject can be readily calculated in real time at up to the framing rate of the 3D camera sensor (for example 30 frames per second). The 3D camera sensor may in certain embodiments also be used to measure head orientation signals of the subject 15. Thus 3D camera sensors such as 44 and 45, determine the biomechanical state of a subject 15 in the field of view of said sensors. However, the range an accuracy of 3D camera sensors may be limited (in one or more directions). Therefore it may be preferable to combine multiple 3D camera sensors, or other combinations of sensors to increase the system range, accuracy and the like.

Referring still to FIG. 1, auditory feedback can be provided to the subject 15 using an arrangement of one, or more, loudspeaker actuators 47, preferably located at various locations surrounding the subject 15. For example, front, left and right sides as well as back. The loudspeakers may in some example configurations, be discrete actuators connected to individual amplifiers and a computer sound card, or a central surround sound processor that includes amplifiers and circuitry well known in prior art.

Alternatively the auditory feedback may be provided using wireless headphones 36 together with optional sound processing controllers and software that synthesize surround sound auditory effect and are well known in prior art. In each implementation, the sound actuators and associated surround sound controllers are connected to the intelligent controller 20.

Auditory feedback may be preferably used to present directional information to the subject 15 during motional training. Directional information may be simply coded into left, right, and center channels, or alternatively, into more complex surround sound coding comprising of multiple sound locations, or the synthesis of the effect of multiple sound locations (known as surround sound processing in the art). Therefore the combination of any auditory feedback mechanism with additional sensors is advantageous, as it is usually necessary to determine the direction that the subject 15, may be facing in order for the intelligent controller 10, to provide subject 15 referenced, auditory directional feedback information. Therefore, combinations of previously described sensors, including inertial sensors, or 3D camera sensors may be used, together with the intelligent controller 20, to determine the subject orientation and provide auditory feedback.

In another embodiment of this invention described in further detail hereinafter, auditory feedback may be provided through spatially distributed, auditory actuator components that are coupled to the subject. In one embodiment, the vibrotactile actuators are designed to produce an acoustic (auditory feedback) signal simultaneous with the tactile stimulus. In general, auditory feedback is provided to the subject 15, by the intelligent controller 20 that is interfaced to the associated audio component hardware controller components.

Visual feedback and instruction can be provided to the subject 15 using one or more displays 34 as set forth in more detail hereinafter. The display should preferably be mounted at a height corresponding to the subject's 15 head level and be on a movable adjustable stand 35. The display 34 is also connected to the intelligent controller 20 and is used to provide visual instruction, cues and feedback during motional training and assessment.

Referring still to FIG. 1, the vibrotactile feedback mechanism 16 mounted on the subject 15 may include an arrangement of vibrotactile actuators as well as a controller and battery. Suitable vibrotactile actuators include the C-2 tactor and EMR actuators available from Engineering Acoustics Inc. (Casselberry, Fla.). The actuators are designed to be wearable on the body and may produce a strong displacement, i.e., vibration, within the frequency range of approximately 30 Hz to approximately 300 Hz. As such, the vibrotactile feedback mechanism 16 uses the sense of touch, i.e., the tactile sensory channel, as a technique for conveying information to the subject 15.

The sense of touch is processed via the somatosensory (SI) cortex in the brain. Various cutaneous sensory regions are mapped to different areas of the SI cortex, making the sense of touch both intuitive and implicitly linked to motion. In other words, the sense of touch is intrinsically linked with the neuro-motor channel, both at the reflex and higher cognitive regions, and is thus uniquely tied to orientation and localization.

Accordingly, the actuators of the vibrotactile feedback mechanism 16 are arranged and coupled to the subject 15, so that the actuators provide body-referenced, spatial information to the subject 15. Any number of actuators may be utilized. In particular, a direction or motion is mapped to a specific vibrotactile actuator, so that activation of the specific vibrotactile actuator and its associated location provide information with respect to that particular direction or motion. Motion may be also conveyed with a vibrotactile feedback mechanism 16 by the sequential and timed activation of a series of vibrotactile actuators, two or more actuators being spatially oriented with respect to the subject, so that the associated location and movement of vibrotactile stimulus provide information with respect to that particular rate and movement direction.

It has been demonstrated that tactile cueing is significantly faster and more accurate than comparable spatial auditory cues and is stable across a variety of body orientations, even when spatial translation is required. The vibrotactile feedback mechanism 16 is therefore an intuitive, non-intrusive feedback mechanism that in certain instances may be more preferable to individual visual and audio cueing. In addition, temporal information can also be conveyed through the actuators in the vibrotactile feedback mechanism 16.

The intelligent controller 20 can be operated to drive the vibrotactile feedback mechanism 16 to provide feedback to the subject 15 during motional training. This feedback may include spatially oriented and body-referenced information, temporal information, information based on sequences or patterns of pulses, as well as information based on vibration frequency. As described previously, the spatially oriented and body-referenced information may include directional information based on the location of the vibrotactile stimulus. The temporal information may be provided according to pulse timing, where more rapid pulses indicate a greater urgency. Information based on vibration frequency may be provided according to high and low frequencies which can be discerned by the subject 15, where frequencies of approximately 250 Hz may, for example, indicate a greater urgency and frequencies less than 120 Hz may indicate less urgency.

The combination of multiple sensory feedback cues in the motional training system 10 is believed to be advantageous for certain subjects. Specifically, combinations of similar feedback cues presented in different sensory modes results in improved task reaction time and accuracy. Sensory integration combines multiple sources of information in motor control, therefore multimodal motional training cues will increase the salience of cues. Further, certain subjects may have deficits in one or more sensory modalities, and multimodal sensory feedback may therefore be more effective than individual sensory feedback configurations. The therapist 40 may interface with the intelligent controller 20 via the additional screen display 30 and the keyboard 31. However, to make it easier for the therapist 40 to monitor and assist the subject 15 during the motional training, the therapist 40 may alternatively use the remote interface 41 to control aspects of the multimodal sensory feedback motional training system 10 as described further below. In other embodiments, the visual display 34 may be used as the therapist interface with the intelligent controller 20, and aspects of the remote interface 41 may be included in the visual display 34, or additional screen display 30, by the inclusion of a touch screen interface.

Figure 2:
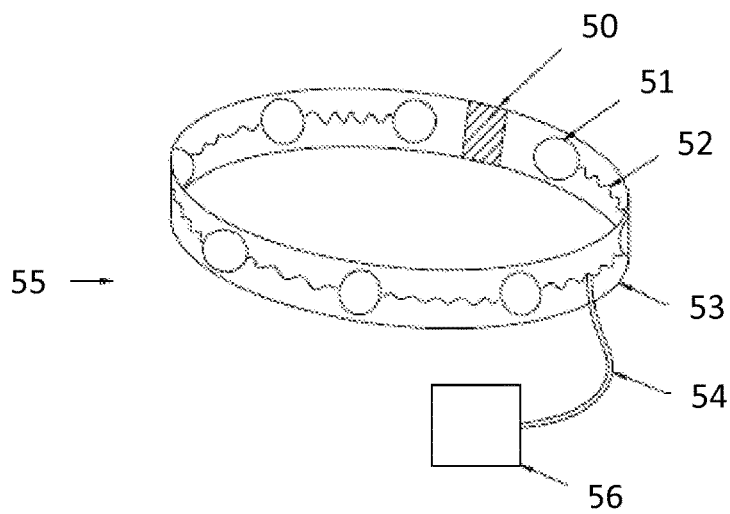
FIG. 2 illustrates an embodiment of a vibrotactile belt according to aspects of the present invention.

An embodiment of a vibrotactile feedback mechanism 16 is illustrated in FIG. 2 as a vibrotactile belt 55 system. The vibrotactile belt 55 may be worn around the torso by the subject 15 as shown in FIG. 1. The vibrotactile belt 55 includes a plurality of actuators 51 that are spaced equally around a band 53. In one embodiment, the vibrotactile belt 55 employs an array of eight C-2 tactors available from Engineering Acoustics Inc. (Casselberry, Fla.). For example, eight actuators may be employed so that when the subject 15 wears the belt, one actuator 51 is centered on the front of the subject 15, e.g., aligned with the belly button. Correspondingly, another actuator 51 is aligned with the spine, another actuator 51 is aligned with the right side of the torso, and another actuator 51 is aligned with the left side of the torso. When the actuators 51 are oriented in this manner, each of the eight actuators 51 may represent a direction relative to the subject 15 similar to the eight major points on a compass, i.e., east, west, north, northeast, northwest, south, southeast, and southwest. Other embodiments may include an array with more or less tactors.

The vibrotactile belt 55, for example, may be formed with a band 53 comprising of a stretch fabric with a fastener 50, which may include a hook-and-loop fastener, button, zipper, clip, Velcro, or the like. A wire, or combination of one or more wires, 52 extends between each pair of actuators 51 and is of sufficient length to allow the band 53 to stretch when worn by the subject 15. In particular, the wire 52 may be looped or coiled and mounted to the belt 55. The actuators 51 are connected to control electronics 56 via a wire harness 54. The control electronics 56 may include a microcontroller with analog to digital converters, circuitry for interfacing with sensors, digital-to-analog converters, and a series of amplifiers. The actuators 51 are optimized for exciting the tactile response by the skin. In some embodiments, the actuators 51 are linear actuators.

This vibrotactile belt 55 may also employ additional sensors, such as direction sensors (not shown), which operate with the control electronics 56 and interface with the system intelligent controller 20, for example via the wireless data connection 21. Additional directional sensors may be used to determine the orientation of the subject 15 with respect to the force plates 11a and 11b to be used by the intelligent controller in motional tasks described hereinafter for the determination of vibrotactile feedback 16. Further, additional directional sensors may be used to determine the orientation of the subject with respect to the therapist 40 and to allow the vibrotactile feedback mechanism 42 on the therapist 40 to indicate the position of the vibrotactile feedback mechanism 16 on the subject. The position of the vibrotactile feedback mechanism 16 may be indicated to the therapist 40 in a format that is independent of or dependent on the orientation of the therapist 40.

Figure 3A:
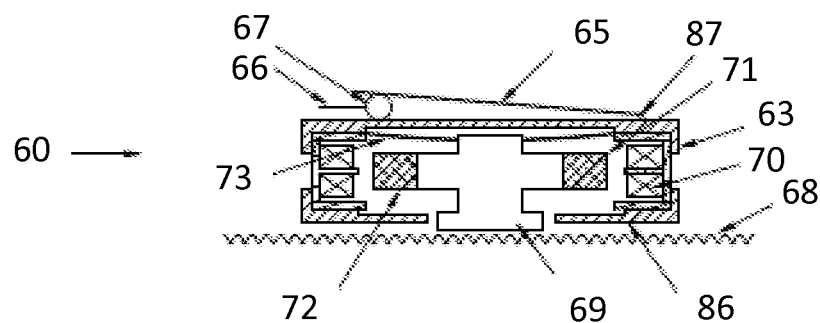
FIGS. 3A-3C illustrate an embodiment of an audible vibrotactile actuator according to aspects of the present invention.

Particular features of a combined vibrotactile and auditory multimodal sensory feedback device and mechanism are illustrated in FIG. 3. The first view 60 shown in FIG. 3A shows a cross section of a concentric electromagnetic vibrotactile actuator design, for example that described in U.S. Pat. No. 7,798,982, together with additional features, 66, 67, 65 and 87. The vibrotactile actuator comprises stator coils 70 mounted within a housing 63, positioned concentric to a permanent magnet 71 ring that is positioned within the housing 63 with various springs 73. The magnet is rigidly attached to a contactor assembly 69 that is positioned in contact with the body or skin load 68. A front portion of the housing 86 is in simultaneous contact with the body or skin load 68. An electrical current flowing in coils 70 will produce a magnetic field that will interact with the permanent magnet ring 72 and displace the contactor 69 into or out of the skin or body load 68. Simultaneously, a thin metal strip 65 is positioned over the rear of the actuator housing, with one side in direct contact with the rear housing 87 and the other side positioned distal to the housing surface using a spacer 67 on an adjustment arm 66. The metal strip 65 will also interact electromagnetically with the changes in magnetic field produced by the actuator and more specifically, the current in the coils 70 and the movement of the permanent magnet 71 attached to the contactor 69. The interaction will cause the strip to move and vibrate and produce sound in accordance with well known acoustic panel physics and electromagnetic (Lorenz and reluctance forces) characteristics. Metal strip 65 is preferably 0.04 mm thickness steel in a rectangular plan-form with dimensions of approximately 30 mm by 15 mm. Spacer 67 is approximately 4 mm in section and is optionally attached to a thin arm 66. The spacer and arm are constructed from a plastic material. Moving the arm 66 towards the center of the vibrotactile actuator optionally increases the bend in the metal strip 65 and thereby changes the amplitude of the metal strip 65 vibration and the emitted sound. Therefore the arm 66 may be used to control the amplitude of the emitted vibration. The arm 66 may also be controlled by a positional actuator such as a motor, solenoid and the like (not shown) and therefore under automatic control from the intelligent controller 20. Sound is therefore produced from the rear of the vibrotactile actuator simultaneous with vibration produced by the contactor 69 acting against the skin or body load 68.

Figure 3B:
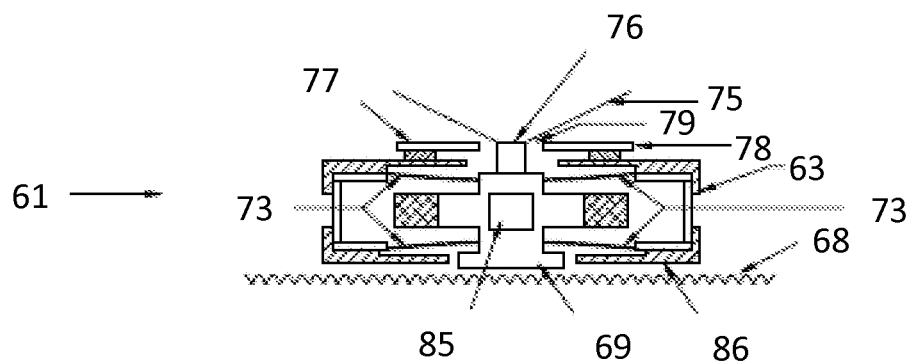

FIG. 3B shows a cross-sectional view 61 of another embodiment of this combined vibrotactile and auditory multimodal sensory feedback device. A panel membrane 75, similar in function and construction to the cone of a loudspeaker, is connected to the vibrotactile actuator contactor 69 at a point close to the center 76 of the membrane 75. A membrane extension 77 may also be optionally used to position the membrane 75 over the contactor 69, or alternatively position the membrane 76 such that the contactor 69 passes moves through an opening 79 clear of the membrane 75. These configuration features can be implemented in a number of vibrotactile actuator designs including designs that actuate the contactor 69 using electromagnetic, pneumatic, piezoelectric and motor 85 designs. Sound is therefore produced from the rear of the vibrotactile actuator upon activation of the vibrotactile actuator; the motion of the membrane 75 is coupled with the simultaneous vibration produced by the contactor 69 acting against the skin or body load 68.

Figure 3C:
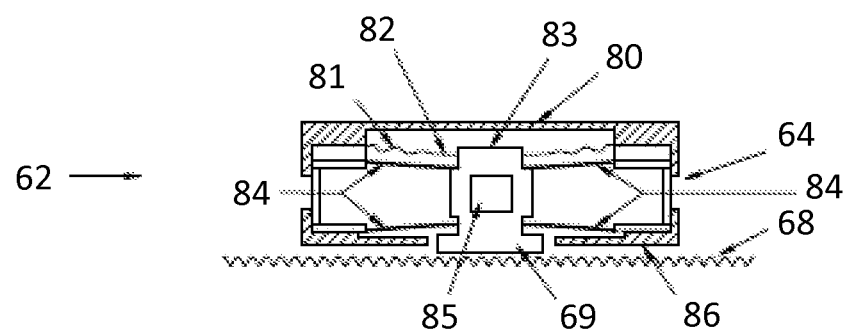

FIG. 3C shows a cross-sectional view 62 of another embodiment of this combined vibrotactile and auditory multimodal sensory feedback device. A panel membrane 82, similar in function and construction to the cone of a loudspeaker, is connected to the back 83 of a vibrotactile actuator contactor 69. The center part of the membrane 82 is connected to the contactor 69 at a point close to the center of the membrane 83. The outer edge of the membrane 82 may be preferentially connected to the inside of the actuator back housing 80 using a compliant surround 81. The membrane 82 therefore is mechanically enclosed within the vibrotactile actuator housing 64 and shielded from any loading effects. However, back housing 80 will act against the transmission and radiation of auditory vibration, therefore gaps in the housing (not shown) to facilitate sound radiation should preferably be made. Further, the housing 64, housing back 80, and membrane 82 design should be such that they provide adequate clearance between the membrane 82 and springs 84. This configuration can be implemented in a number of vibrotactile actuator designs including designs that actuate the contactor 69 using electromagnetic, pneumatic, piezoelectric and motor 85 designs. Sound is therefore produced primarily from the rear of the vibrotactile actuator upon activation of the vibrotactile actuator; the motion of the membrane 82 is coupled with the simultaneous vibration produced by the contactor 69 acting against the skin or body load 68.

Other alternate embodiments of a combined vibrotactile and auditory multimodal sensory feedback device include acoustically resonant elements that are attached to the moving contactor in vibrotactile actuators, and are designed to resonate at the drive frequency of the vibrotactile actuator. Further embodiments include separately powered (driven) piezoelectric loudspeakers and the like, that are integrated onto the back housing of vibrotactile actuators or positioned in close proximity (for example adjacent) to the vibrotactile actuators. Closely located separately powered loudspeakers may require additional amplifier drive circuitry which may be included in the controller 56.

Figure 4A:
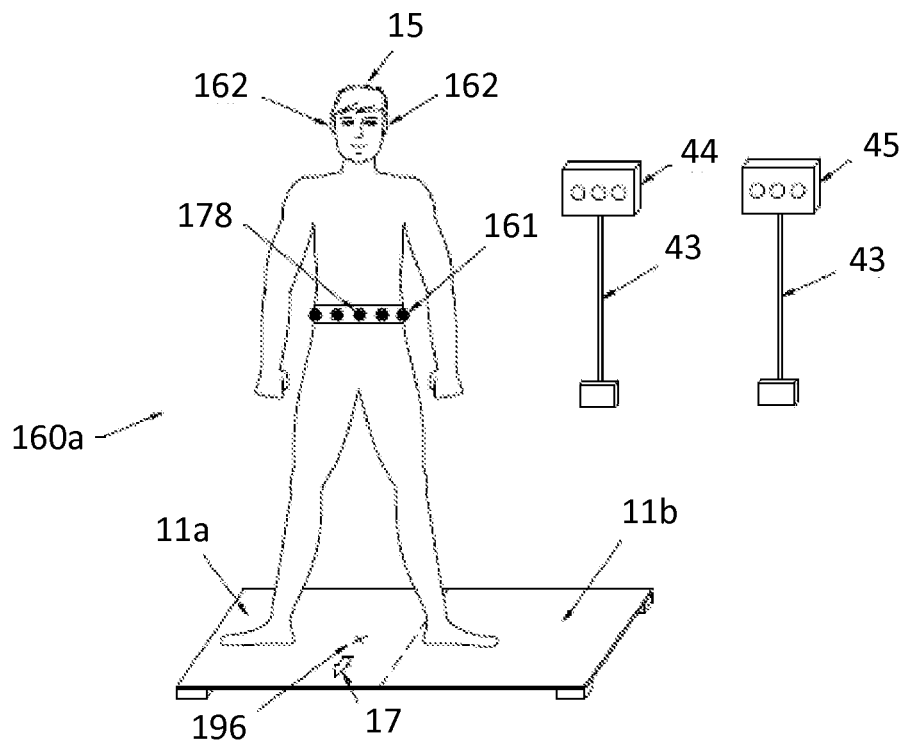
FIG. 4A-4C illustrate multisensory feedback according to particular aspects of the present invention.

FIG. 4 further illustrates information relating to the combined vibrotactile and auditory feedback mechanism 161. In FIG. 4A, the view 160a shows the subject 15 facing in a particular direction represented by the arrow 17, whilst standing on force plates 11a and 11b, together with a combined vibrotactile and auditory feedback mechanism 161. One or more 3D camera sensors (44 and 45), provide an instrument for measuring body sway as well as the biomechanical features such as, joint positions and angles of the subject 15 who is standing within the field of view of one or more 3D camera sensors. As described hereinbefore, the 3D camera sensors (44 and 45), the vibrotactile feedback mechanism 16, and the optional inertial sensors 12 and 13 may communicate with the intelligent controller 20 via conventional wired or wireless connections. Further, the multimodal sensory feedback motional training system can be made up of various individual, or combinations of sensor elements depending on the application and motional task requirements. In each case the COP 196, COG, trunk sway or related biomechanical features may be measured and used by the intelligent controller 20 to determine the postural characteristics and state of the subject 15.

The combined vibrotactile and auditory feedback device 161 is coupled to the subject 15 and located together with vibrotactile actuators that are spatially located on a belt (around the torso). The vibrotactile actuators may be actuators that have been modified or designed, as described hereinbefore, to produce auditory signals simultaneously with vibrotactile vibrations. In certain embodiments, it is also possible to select to only produce auditory signals or vibrotactile vibrations if only one of the modes is required at a particular stage of motional training. This mode may be further automatically selected by the intelligent controller without necessarily requiring any configuration on the part of the therapist or subject.

The vibrotactile and auditory feedback actuators are spatially arranged around the torso of the subject, therefore, as each vibrotactile and auditory feedback actuator is activated, the subject 15 will perceive a sound corresponding to that particular spatial location, determined by acoustic information detected by the subject's ears 162. Auditory feedback and the location of the auditory sound source are in this example, presented simultaneously with the information perceived via the vibrotactile sensory perception channel; in other words multimodal sensory feedback has been provided to the subject. Specifically, it should be evident that sounds radiating from the combined vibrotactile and auditory sensory feedback device will be perceived as being located within the same region as the vibrotactile spatial location. As a specific example, sounds radiating from the front tactor 178 would be perceived by the subject 15 as coming from front and corresponding to navel. This type of multimodal sensory feedback is termed congruent (as each mode is presenting equivalent information) as is believed (in certain motional training cases) to be more reliably and rapidly interpreted by the subject 15.

Figure 4B:
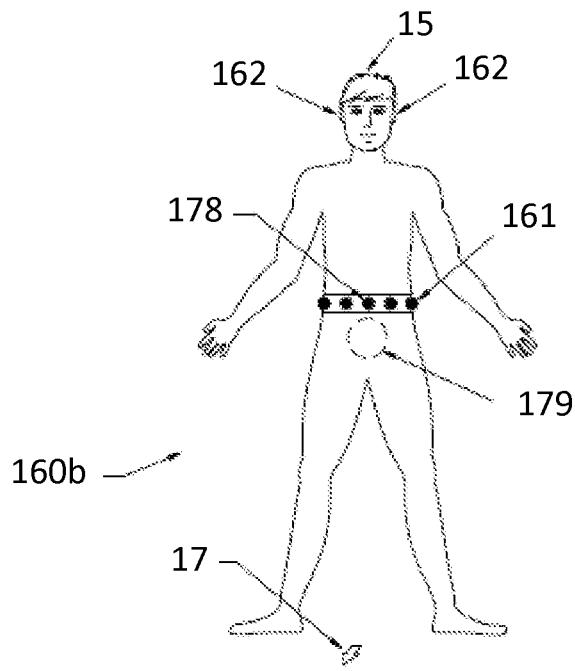

FIG. 4B, shows further details of components in an embodiment of the multimodal sensory feedback motional training system. Specifically, view 160b shows the subject 15 with an inertial sensor 179 that is mounted onto the lower back of the subject, as well as a vibrotactile and auditory feedback mechanism 161 that is coupled to the subject 15. The inertial sensor 179 measures the direction, indicated by arrow 17, that the subject 15 is facing. The inertial sensor may be individually used to determine the COG, or related postural sway characteristics of the subject 15, or used in combination with other sensors as described hereinbefore. The vibrotactile actuators may be actuators that have been modified or designed, as described hereinbefore, to produce auditory signals simultaneously with vibrotactile vibrations. The vibrotactile and auditory feedback actuators are spatially arranged around the torso of the subject. Therefore, as each vibrotactile and auditory feedback actuator is activated, the subject 15 will perceive a sound corresponding to that particular spatial location, determined by acoustic information detected by the ears 162.

The operation of the multisensory feedback motional training system 10, generally relates to the subject 15 attempting to move according to one or more motions defined as a part of the motional training, e.g., moving from a sitting position to a standing position to test static balance. These predetermined motions may make up all or part of a functional activity. One or more sensors (such as force plates, 3D camera sensors, inertial sensors as described hereinbefore) measure the attempt by the subject 15 to move according to the predetermined motions. In particular, the 3D camera sensors determine corresponding subject 15 physical position in space and any associated movements. The intelligent controller 20 then determines the biomechanical state of the subject 15, for example the COG, COP, biomechanical joint positions and angles. If the intelligent controller 20 determines that the biomechanical state measure (for example COG) has moved beyond a threshold, the intelligent controller 20 activates one or more sensory feedback elements that correspond to the segment. Thus, the subject 15 receives a sensory stimulus (for example vibrotactile and auditory), or feedback, when there is a variance between the location of the biomechanical state measure and the predetermined movement threshold.

Figure 4C:
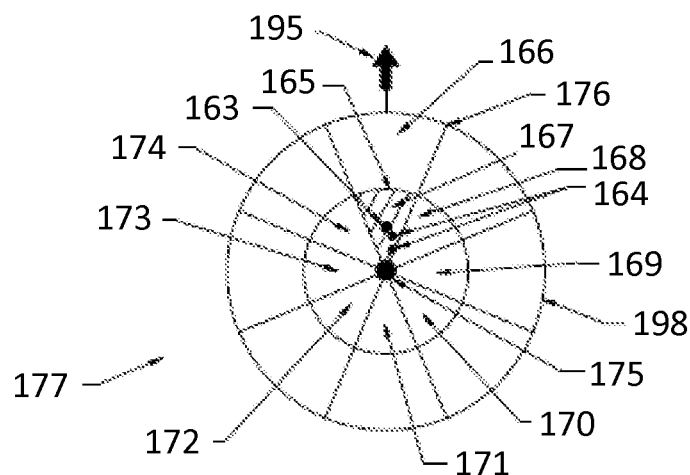

FIG. 4C illustrates a depiction of a visual feedback screen display 177 that may be shown by the intelligent controller 20, on the display monitor 30, or subject visual feedback display screen 44. FIG. 4C also illustrates as an embodiment of this invention, the means for calculating the subject's postural characteristics, detecting and quantifying a variance from pre-set parameter limits and representing this as multimodal feedback to the subject.

The screen display provides a view 177 that shows the biomechanical state measure 163 that represents the current postural characteristics associated with the subject 15. In certain embodiments, the measure 163 may be the center of pressure (COP) as determined via the force plates 11a and 11b or derived from combinational sensors as described hereinbefore. In other embodiments, the screen display may also provide a view 177 that shows the biomechanical state measure 163 being derived from the center of mass (COM), or ground projected COG, as determined by one or more inertial sensors or 3D camera sensors as described hereinbefore. In each embodiment, the biomechanical state measure (COP or COM), may be shown on the display in real time as a current data sample point 163, together with a sequence of previous samples 164. Therefore view 177 provides a visual indication of the time history of postural movement characteristics associated with the subject's 15 postural movements, as represented by data sample point 163. In other words, visual sensory feedback is provided on display view 177 which may be used by the subject 15 to assist with the performance or accuracy associated with a functional motional training task.

The view 177 also shows a training region that corresponds to an area 166 in which the subject is expected to perform a predetermined motion as a part of motional training. Accordingly, the view 177 may be presented on screen display 34 and may be used to monitor activity by the subject 15, and to provide visual feedback to complement the information provided by the vibrotactile feedback mechanism 16 and the auditory feedback 47, or 36, or combined vibrotactile and auditory feedback mechanism 161. In addition, the screen display view 177 may be employed to set parameters or thresholds for operation of the multimodal feedback mechanisms.

In FIG. 4C, the view 177 shows a series of eight segments, or zones, 167, 168, 169, 170, 171, 172, 173 and 174, around the center 175. The center 175 is usually calibrated and aligned to correspond to the zero or correct postural alignment of the subject 15. For example in steady stand, this would correspond with stable vertical upright posture; and the COM and COP would be equivalent. Software features in the intelligent controller 20 allow the therapist or user to set and reset this at various stages during the motional therapy, for example, at the start of a particular functional motional activity task. Thus before operation, the biomechanical state measure data point 163 and center 175 is initially zeroed, or reset, to align the center 175 and the segments over the biomechanical state measure data point 163. However, the center 175 may also be zeroed after a subset of the predetermined motions during the motional therapy. The therapist 40 may zero the center 175, for example, via the therapist remote interface 41 while monitoring the subject's attempt to perform a set of predetermined motions. The motional training system 10 allows the subject 15 to sequentially move from one region to another according to the set of predetermined motions, e.g. from a sitting position to a standing position and so on. Zeroing allows to each region, i.e., a subset of the predetermined motions. Otherwise, the thresholds would only apply to the set of predetermined motions as a whole.

The subject 15 is facing in a direction indicated by the arrow 17 in FIG. 4A and this corresponds to the vertical arrow 195 shown in FIG. 4C. Each segment corresponds to an actuator 51 on the previously described vibrotactile feedback mechanism 16 or combined vibrotactile and auditory feedback actuator 161. In the embodiment of FIG. 4, there are eight segments corresponding to eight actuators on the combined vibrotactile and auditory feedback mechanism 161. The combined vibrotactile and auditory feedback mechanism 61 may be oriented so that one of the eight actuators 78 is centered on the front of the subject 15, another actuator is aligned with the spine, another actuator is aligned with the right side, another actuator is aligned with the left side, and the remaining four actuators are aligned and located between the actuators (i.e. similar to the cardinal and ordinal points on a compass). Therefore, the segment 167 shown in FIG. 4C may correspond with the actuator 78 on the front of the subject, the segment 171 may correspond with the actuator aligned with the spine, and segments 169 and 173 correspond with the actuators on the right and left sides, respectively. Each segment includes an arc that represents an adjustable threshold for each corresponding vibrotactile actuator. For example arc 165 represents an adjustable threshold for segment 167 and actuator 78. In other words, the width of the arc as well as the length of the segment may be configured to set thresholds that determine when the actuators are activated to provide feedback.

The biomechanical state of the subject 15 can be measured using force plate sensors 11*a* and 11*b*, inertial sensors 179, 3D camera sensors, or combinations of these sensors as described hereinbefore. In various embodiments, the COP or COM calculated by the intelligent controller 20 and associated sensors can be depicted in real time on the graphical representation illustrated in FIG. 4C, typically as biomechanical state measure data sample point 163. If, for example, the biomechanical state measure 163 data sample point of the subject 15, moves to a region beyond a segment 167 and arc 165 (therefore reaching region 166), the corresponding vibrotactile actuator 178 (and associated auditory stimulus) may be activated. In other words, when there is a variance between the determined location of the biomechanical state measure sample point 163, and preset threshold limits, an actuator (and display) is activated and feedback is therefore provided to the subject 15. Thus, the segments 167, 168, 169, 170, 171, 172, 173 and 174 and their corresponding arcs may correspond to thresholds that define the boundaries for movement by the subject 15. The thresholds are selected so that information regarding movement of the subject relative to these thresholds provides useful information during motional therapy. It is noted that movement of the biomechanical state measure sample point 163 can be caused when the subject sways, and movement by foot or other significant movement is not required. As such, the example embodiment illustrated by FIG. 4 can assess static balance. Further, if the anterior posterior threshold limits such as segment 167 and 171 are increased, dynamic forward/backward motion may also be measured. Similarly, if inertial data is used as described hereinbefore, the sensor information can be used during dynamic motions such as gait, steps, lunges, and postural transitions (such as sit to stand).

During an example operation of the motional training system 10, the subject 15 attempts to move according to one or more motions defined as a part of the motional training, e.g., moving from a sitting position to a standing position to test static balance. These predetermined motions may make up all or part of a functional activity. The various combinations of sensors, force plates 11*a* and 11*b*, 3D camera sensors and inertial sensors 179, together with the intelligent controller 20, react to the attempt by the subject 15 to move according to the predetermined motions. For example, the force plates 11*a* and 11*b* determine corresponding movement of the biomechanical state measure sample point 163 (in this case COP) and communicate this information to the intelligent controller 20. As discussed previously, thresholds may be visually defined on the display monitor 30 or 44 via the intelligent controller 20 in terms of segments 167, 168, 169, 170, 171, 172, 173 and 174 and corresponding arcs. In one embodiment, if the intelligent controller 20 determines that the biomechanical state measure sample point 163 has moved beyond any of the segments and past any of arcs, the intelligent controller 20 activates the actuator corresponding to the segment. Thus, the subject 15 receives a vibrotactile stimulus, or feedback, when there is a variance between the location of the biomechanical state measure data sample point 163 and the segments and the arcs.

It is preferable to indicate feedback to the subject 15 using system, or therapist selected, combinations of multimodal sensory feedback displays. Therefore visual feedback may be provided to the subject using the screen 44 and view 177, tactile feedback may be provided using a vibrotactile belt 16, and auditory feedback may be provided using combined vibrotactile and auditory feedback actuator 161 or using one or more loudspeakers 47. Combined vibrotactile and auditory feedback using actuator 161 naturally maps the same feedback to both the vibrotactile and auditory sensory pathways.

Visual feedback may show changes in salient visual features to illustrate variance and feedback. For example, in one embodiment, the biomechanical state measure data sample point 163 may change color as it moves beyond a threshold. Other examples include shading the segment area with a different color or texture to illustrate the boundary and threshold for feedback.

Auditory feedback using a combination of discrete loudspeakers can in one embodiment of the invention, be used to map location sound location and audio salient features (such as intensity, pitch changes and pulse rate changes) to the location and extent of variance.

The predetermined motions corresponding to a functional activity may require the subject 15, and thus the biomechanical state measure sample data point 163, to move from one area on view 177 to another. Accordingly, in some embodiments, vibrotactile cueing may be employed to guide the subject 15 to a specific target area. For example, using the multimodal sensory feedback motional training system 10, the subject 15 may be encouraged via vibrotactile cueing to move his COP or COM and biomechanical state measure sample data point 163, until it reaches a previously identified target zone area such as the region 166 (depicted in FIG. 4C). Vibrotactile cueing may initially activate the actuator 178 that corresponds to the segment facing the target 167. Once the target region 166 (for this particular example) has been reached, the therapist 40 may also elect to move the center 175 to the new location, or zero the axes to this new end location. Alternatively, the therapist may elect to guide the subject to a new target, for example, the new target may be the initial starting position.

Vibrotactile feedback may be preferably comprised of pulses may be modulated by the variance. For example, the vibrotactile feedback with a frequency of 250 Hz and duration of 300 ms may be pulsed initially at 0.1 Hz, pulsed at 1 Hz at higher variances, and then pulsed at 5 Hz when the data sample point reaches a location corresponding to a maximum variance. The variance and rate of change of variance is calculated by the intelligent controller 20, and may also be used to optimally apply rate based vibrotactile feedback to the subject 15 during motional training and consequent biomechanical state measure movement. For example, the variance, or rate of variance, can be partitioned into discrete bands (or "bins") with upper and lower thresholds, that correspond to a particular tactile feedback level. As the variance increases, tactile feedback patterns can be provided that have salient characteristics that correspond to an increase in urgency. Pulse rate and tactile vibration amplitude (especially rise time) are our identified salient features that correspond to urgency. Typical pulse rates may have ON tone-burst lengths of between 10 and 800 ms.

In another embodiment, the calculated rate of change of variance may be used to optimally apply rate based vibrotactile feedback to the subject 15 during motional training and consequent biomechanical state measure (for example COP) movement. As the rate of change of variance increases above a preset threshold, corresponding tactile feedback activations comprising of patterns can be activated. These tactile patterns have salient characteristics that correspond to an increase in perceived urgency. For example, therefore the rate of change of variance can modulate tactile activation via discrete linear limits; low normalized rate of change of variance fires, or activates, at 250 ms on 50 off, medium normalized rate of change of variance fires at 250 ms on 25 ms off and high normalized rate of change of variance fires at 125 ms on 25 ms off. In another example we activate tactors with tone-burst pulse repetition rates that depend on the rate of change of variance. If the biomechanical state measure (for example COP) location is greater than a preset threshold, rate of change of variance is used to modulate the tactor tone-burst repetition rate directly. For example an initial tactile pulse repetition sequence may start at 400 ms on, 50 ms off, and progress proportionally to a maximum rate of 50 ms on 50 ms off at the highest rate of change of variance.

Figure 5:
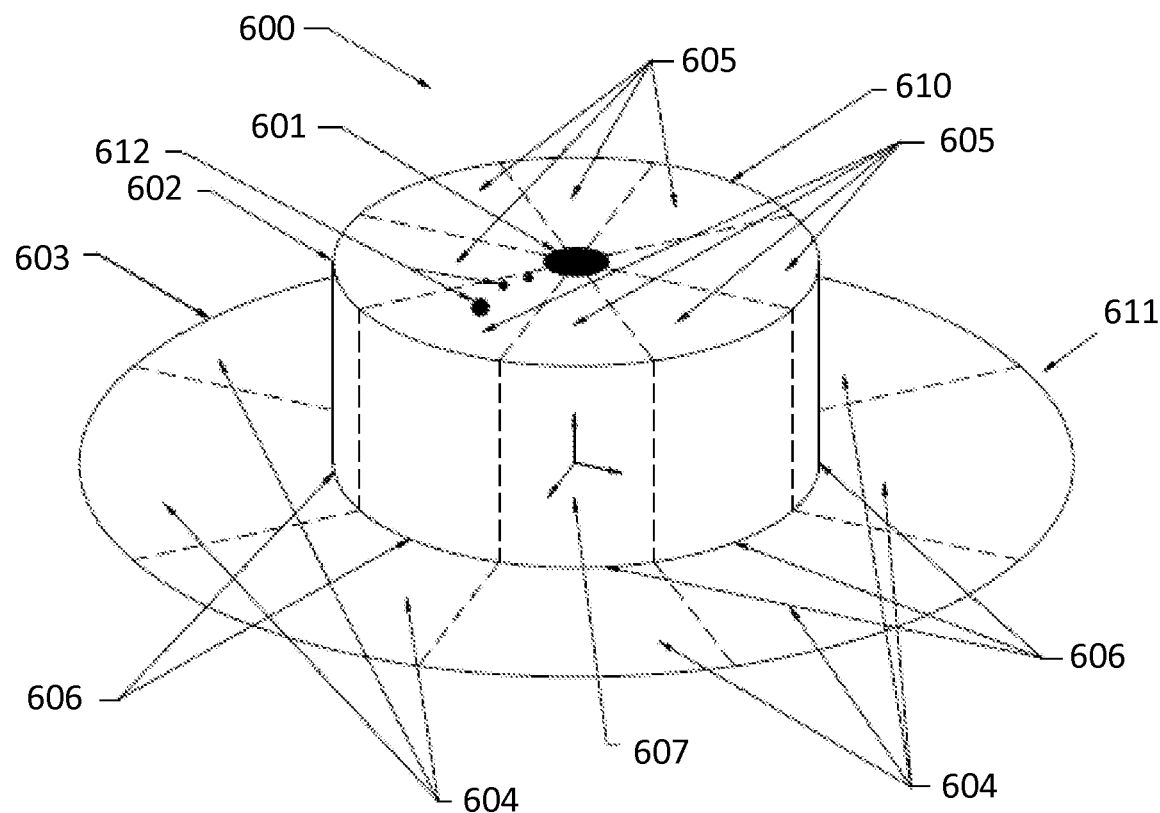
FIG. 5 illustrates another embodiment for a visual feedback display according to aspects of the present invention.

FIG. 5 illustrates an alternate view describing similar information to that presented in FIG. 4C (top down view). FIG. 5 illustrates a depiction of perspective view screen display that may be shown by the intelligent controller 20 on the display monitor 30 or subject visual feedback display 34. FIG. 5 also illustrates as an embodiment of this invention, an alternate means for calculating the subject's postural characteristics, detecting and quantifying a variance from pre-set parameter limits and representing this as multimodal feedback to the subject. The perspective screen display provides a view 600 that shows the biomechanical state measure (for example the center of pressure (COP)) of the subject 15 as determined via the force plates 11a and 11b or derived from combinational sensors as described hereinbefore. The screen display may also provide a view 600 that shows the center of mass (COM), or ground projected COG, as determined by sensor combinations as described hereinbefore. In each embodiment, the COP or COM, may be shown on the display in real time, as a biomechanical state measure data sample point 601. A sequence of successive previous biomechanical state measure data point samples 612, together with the most recent data sample point 601, may alternately be depicted to give a visual indication of the time history of postural movement characteristics.

The view 600 shows two regions, the first 610 corresponds to a raised area, and the second, a lower area 611 outside the raised area 610. As described previously, the subject is expected to perform a predetermined motion as a part of motional training. Accordingly, the view 600 may be presented on screen display 34 and may be used to monitor activity by the subject 15, and to provide visual feedback to complement the information provided by the vibrotactile feedback mechanism 16 and the auditory feedback 47, or 36, or combined vibrotactile and auditory feedback mechanism 161. In addition, the screen display view 600 may be employed to set parameters or thresholds for operation of the multimodal feedback mechanisms.

As described previously, there are eight segments 605 within raised area 610 and similarly, eight sections of segments 604 within the lower area 611 region. The transition between the raised area 610 and lower area for each particular segment is represented by the segment arc boundary 606. The arc boundary 606 can be set by the therapist (or user) during multimodal sensory feedback motional training activities.

During motional training activities it is advantageous to first calibrate and zero the display center 607 to be the same as the initial subject COP or COG. The biomechanical state measure data sample point 601 will then be initially at the same location as the display center 607. Postural movements that result in the biomechanical state measure data sample point 601 remaining within raised area 610 will then typically not produce a variance and therefore any additional vibrotactile or auditory feedback (visual feedback is provided through the movement of the data sample point). However, if there are postural movements that result in the biomechanical state measure data sample point crossing any of the transitions 606 a variance is produced and vibrotactile and or auditory feedback is given as described previously.

Visual feedback is then provided by a discontinuous "fall" in the biomechanical state measure data sample point 601 from the raised area 610 to the lower area 611 until such time as subject postural motion causes the subjects biomechanical state measure data sample point 601 to return to the raised area 610. In other embodiments, visual feedback may also be associated with various screen and component color changes, associated with the lower area 611 and raised area 601 and the location of the biomechanical state measure data sample point 601.

It is generally known that for subjects with vestibular deficit, moving their head during postural tasks greatly increases the difficulty of the motional task. Therefore, injured subjects may be inclined to only move their head within a narrow zone so as to preserve their stability and oscillopsia or "blurring" of the visual world is often associated with head movements, and is an important part of the overall disability of the subject. Visual blurring is usually due to the inability of the vestibulo ocular reflex (VOR) to maintain gaze stability during said head movements. Retinal slip, due to the images "slipping" off of the fovea, is widely regarded as the primary mechanism underlying degraded dynamic visual acuity, although other neurological system injury and deficits may also play an important role.

In this embodiment of the invention, we provide a motional training environment in which head movements, together with multimodal sensory feedback are used as part of various vestibular ocular therapeutic activities, or as part of an assessment protocol.

As described hereinbefore, gaze stabilization is an important part of VOG rehabilitation. This process requires the subject to move their head, through different movements, whilst their gaze remains fixed on a visual target. The exercises must be repeated and adjusted (by the therapist) to increase the challenge (including dual task or distractions) and applicability. However, since this activity typically induces effects of nausea in the subject, it is difficult for most injured subjects to comply with this activity and therefore the therapist must be able to closely monitor the subject compliance.

Figure 6:
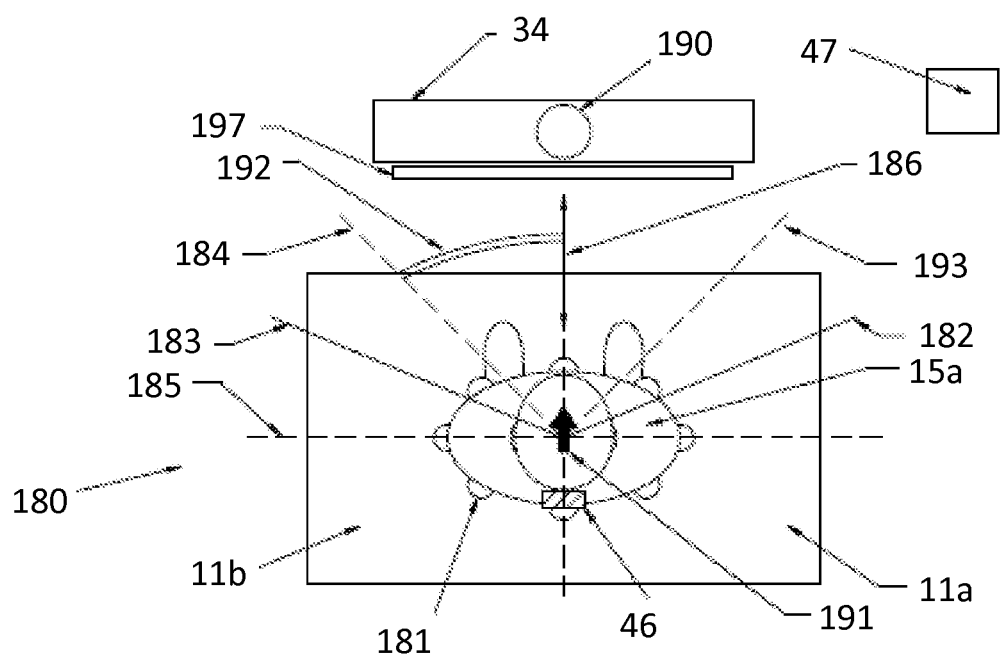
FIG. 6 illustrates aspects of a multimodal sensory feedback motional training system according to aspects of the present invention.

Therefore it is an object of this embodiment of the invention to provide a system and methods for a providing multisensory feedback during therapy, methods for providing graduated transitional (dynamic) visual motion, and visual feedback motional training configurations for vestibular ocular system recovery. It is a further object of this embodiment of the invention to provide a system and method for the assessment of the subject's vestibular ocular capability and the subject's compliance with transitional motion and visual tasks, during vestibular ocular therapy. FIG. 6 illustrates a top-down view 180 of a multimodal sensory feedback, vestibular ocular assessment and therapy system. The view 180 shows the subject 15*a* who is wearing a vibrotactile belt 181 and is standing in front of a visual feedback display screen 34. In one embodiment, a head worn inertial sensor 46, is used to measure the head orientation and position of the subject 15*a* and provide this data to the aforementioned intelligent controller 20. In an alternate embodiment, the orientation and position of the head can be measured using image processing techniques and a camera 190 mounted on the screen 34. In further embodiments, said camera 190 may be an aforementioned 3D camera sensor, that is used to determine the head orientation and position (and other biomechanical state and characteristics) of the subject 15*a*. The camera image and related sensor information is processed by the intelligent controller 20. For example, known facial features extraction algorithms may be used together with known triangulation algorithms for the determination of the subject's 15*a* head orientation in three dimensional space. In other alternate embodiments, reflectors may be used on the head of the subject 15*a* to provide a simple feature reference for the camera image head orientation and location algorithms. In this particular embodiment, it is beneficial to use IR sensors.

In another embodiment, an eye tracking system 197, known in prior art (exemplary devices include EyeTrak, Tobii and Mirametrix systems), may be used to measure the subject 15*a* gaze position on screen 34. This is advantageous as persons with vestibular ocular deficits typically experience more involuntary eye movements, such as blinking, during times in which a visual target is perceived to be out of focus. Therefore an eye tracking system 197 provides a measure of the subject's 15*a* actual eye gaze vector (rather than head gaze vector 191), and a measure of the occurrence and duration of blinks. Eye tracking systems are camera based and include image processing systems for identifying and tracking the eye ball. Therefore it is recognized that eye tracking features may be included in embodiments using camera 190 and 3D camera sensors. As described hereinbefore, the biomechanical state and characteristics of the subject 15*a* may be determined using one or more combinations of aforementioned sensors (force plate, inertial or 3D camera sensors). For example, the postural characteristics of the subject 15*a* can be measured using one or more force plates, 11*a* and 11*b*, or using only an inertial sensor that is mounted on the back of the subject. The vestibular ocular assessment and therapy system shown in view 180, therefore has additional sensor and system capability for the simultaneous measurement of the subject's 15*a* head orientation, and in some embodiments, capability for tracking the subject's 15*a* eye gaze.

FIG. 6 provides a means for providing multisensory feedback during subject 15*a* head movements. As described previously, the head rotation and position can be measured using the data provided from a head worn inertial sensor 46, or other previously described sensor combinations. For example, if the subject is instructed in a predetermined motional activity to move their head side to side, the head gaze vector 191 will move through a range of angles (measured by said sensors) during the side to side head movement. For example angle 192 will be measured between the forward gaze vector 191 (facing forward 186) and an extremity position 184. Similarly, another extremity position 193 is depicted for head rotations towards the right side of the subject. Extremity positions 184 and 193 can be preset and used as target goals for the subject head movement during a particular functional task. Further, angle 192 describes the rotational motion of the subject's 15*a* head during this motional activity.

Preferably, auditory feedback should be provided to the subject 15*a* when the gaze vector 191 reaches the target goal (extremity point 184 and 193). Audible feedback should be preferably provided through previously described wireless headphones 36 that are worn by the subject 15*a*, although a separate set of one or more discrete sound sources 47 may also be used in other embodiments, or other configurations such as a wired headset may be implemented. In other embodiments, aforementioned a combined vibrotactile and auditory sensory feedback device, or combinational actuator 161 may be used to provide both auditory and vibrotactile feedback. For configurations utilizing one or more discrete sound sources, the sound sources should preferably be located on an axis 185 that closely corresponds with the medio-lateral axis of the subject 15*a*. The auditory feedback should produce a short tone (for example; 800 Hz, 50 ms duration, sound pressure level SPL 83 dBA) when the head rotation reaches a predetermined limit set by a predetermined angle 192 or extremity position 184 or 193. Preferably, auditory feedback should also correspond to the side towards which the head is turning. Therefore by way of example, auditory feedback should be presented to the headphone, or discrete sound source such as, for example and not by way of limitation, loudspeakers, corresponding to the left ear as soon as the head is rotated past limit 184 and similarly to the right ear when the head is rotated past the predefined limit 193 that may be set for the associated right side.

Other motional training head movements such as up down (nodding), diagonal and ear to shoulder can also be implemented in this activity. Collectively, side-to-side, up-down and diagonal head movements are referred to as headshake. In each headshake movement, the head worn inertial sensor 46 (or sensor selected) provides a measurement of the head position and orientation which can be used by an intelligent controller to calculate the relative head position and provide the subject with feedback guidance via an associated auditory tone once a predefined head positional threshold has been reached.

In alternate embodiments of this invention, tactile feedback or visual feedback can be provided to the subject 15a when the gaze vector 191 reaches the target goal (extremity point). Preferably, tactile feedback should also correspond to the side towards which the head is turning. Therefore by way of example, tactile feedback should be presented to the tactor corresponding to the left side as soon as the head is rotated past limit 184 and similarly to the right side when the head is rotated past the predefined limit 193 that may be set for the associated right side. While this is described configuration, it is not to be construed as a limitation of the system and method of the invention, as the location and numbers of tactors used in this mode of feedback is entirely a matter of preference of the user.

The limits 184 and 193 should be configurable and are usually preset by the therapist to meet the needs of a particular subject. Further, the head movement task may be made more difficult by changing said limits to positions that require the subject 15a to extend their head rotation. For example, new limits 183 and 182 may be set to make a more challenging head rotation task.

It is known in the art that rehabilitation exercise repetition may lead to habituation and compensation due to internal recovery mechanisms such as brain plasticity and the development of alternate mechanisms that compensate for the original injury or vestibular deficit. FIG. 6 describes a system for providing graduated transitional visual motional training and assessment activities to the subject, especially for the treatment (or assessment) of vestibular ocular dysfunction. The system in particular, addresses the compensation, adaption and habituation of the vestibular ocular system, by providing visual exercises that are linked to transitional head movements. In each visual motion training and assessment activity (described in detail hereinafter), head movements are simultaneously associated with visual feedback components that are provided on one or more screen displays 34, located in front of the subject 15a.

Multimodal sensory feedback is a particular feature of the visual motional training system 180. As described hereinbefore, various sensors measure the biomechanical state and characteristics of the subject 15a during motional training. Further, sensor information together with an intelligent controller assesses one or more of the biomechanical state measurements and determines if there is a variance between the actual postural variables and predetermined limits. If there is a variance, one or more combinations of multisensory feedback is provided to the subject 15a, which will typically be internally processed by the subject as sensory augmentation information, and used to estimate new postural and motor control parameters in order to reduce or correct said variance. Further, it is beneficial in advance of, and during visual motional training, to provide vibrotactile postural feedback. As described previously, a torso worn vibrotactile belt 181 may be used to provide body referenced feedback. For example, vibrotactile feedback may be preferentially given during these head movement therapy tasks based on the variance, or rate of chance of variance, between the instantaneous COP and preset limits. This vibrotactile feedback acts to improve the postural control of the subject 15 who may be standing on force plates 11a and 11b. In certain instances where postural control is particularly poor, it is advantageous to first apply vibrotactile feedback to a subject 15a who is seated on a chair positioned on said force plates. This provides a motional training opportunity whereby the subject 15a need only to control their upper body postural movements (which is simpler than standing). Once seated and standing postural control is adequately demonstrated by the subject 15a, the motional training may progress to visual training and vestibular ocular adaptation exercises.

Referring now to FIG. 7 which shows various features and embodiments of this invention regarding the visual display 34 and methods for providing a visual scene or background, and visual feedback to the subject 15a. FIG. 7A shows a view 200 that may be shown during therapy or assessment. The display is usually designed to cover a large portion of the screen 34 and therefore presents a significant field of view 204 to the subject 15a. Two visual objects are provided, the first 201 is a visual marker on which the subject should attempt to fix their gaze during a first embodiment of this visual motional training activity. The second visual target 202 may be a transient target that must be identified by the subject, and may appear at any random location on the display 203. During assessment, the time to respond and the number of correctly identified targets would be used as a basis for a functional visual acuity test. The target 202 in this embodiment may be shown for short durations, for example 20 ms to 5 seconds. Decreasing the target 202 onscreen duration increases the difficulty of the task. Increasing the screen distance between marker 201 and target 202 increases the difficulty in an object identification task.

Dynamic visual acuity can similarly be evoked by providing auditory feedback and instructions regarding simultaneous head movement during the activity. In this case, the subject 15a is instructed to move their head between predefined limits with associated auditory feedback as described hereinbefore. In a dynamic visual assessment activity, it is particularly important to standardize the rate and extent of head movement. Auditory feedback can again also be given for head movement rates that are within the correct range. For example, if the head movement is within 1-2 Hz, a particular assessment activity would record the dynamic postural data, the head movement data and provide auditory feedback. If the head movement rate were to fall below 1 Hz, a low hum or different set of auditory feedback can be given indicating to the subject and therapist that the test requirements have not been met. In another example, the limits may be set to head movement rates above 2 Hz challenging the vestibular system. It is further desirable to vary the visual target 202 and have the subject report on identifying characters or shapes during this activity.

In another visual feedback motional training and assessment embodiment, target 202 may be represented by an enclosed area (for example the interior of a box). The subject is required to move their head position to control the screen position of visual marker 201 such that visual marker 201 is located within target 202. In other words, the visual marker 201 must be "captured" by the target 202. Therefore in this embodiment, visual marker 201 provides feedback regarding the subjects head gaze vector 191, as measured by inertial sensor 46 (or other sensor combinations as described hereinbefore). The intelligent controller 20 processes the head gaze vector and may low pass filter the signal, to remove high frequency noise components (and thereby remove visual jitter) before depicting it on a depiction of the visual field area 203. Visual target 202 may be scaled in size (and area) in order to make the task simpler. Further, there is a system gain between head movements and the resultant movements of the visual marker 201 on the screen. The gain can be greater or less than unity and is configurable by setting appropriate parameters in the intelligent controller 20. This gain may be increased or decreased to make the task difficulty vary. The visual target 202 may also move dynamically to other areas in the visual field 203. In this case the subject 15*a* must move the visual marker 201 by controlling their head movements, and follow (or capture) the target dynamically. It is desirable to make the dynamic movements follow according to scalable steps in movement rate and extent; in other words, graduated transitional dynamic visual motion.

In this visual feedback motional training task, the position of target 202 and visual marker 201 signals describe aspects of the actual performance of the subject during this task, and therefore may be used as an assessment measure. Each signal component will also be associated with one or more limit parameters that are based on the defined visual target 202 size. If the signal exceeds said limit parameter, a variance occurs. As described hereinbefore, the variance may be used to provide feedback; for example, auditory feedback regarding the error. In this assessment embodiment of the invention, the variance between the parameter (the expected value) and the measured signal may also be preferably used as a measure of the subject's performance. Measured and identified characteristic features will be associated with the predetermined intended task and a variance may exist between ranges of intended features versus the actual subject data. This variance may be also derived into a rate of variance, and may be used as a basis during therapeutic activities to calculate thresholds and conditions for vibrotactile feedback to be presented to the subject. In another embodiment of this invention, the calculated variance is used as a direct measure of the subjects movement error during the act of completing the task and can therefore be used as a score of the subjects performance. More specifically, the greater the number of variance occurrences and the higher the magnitude of cumulative variance the poorer the performance. Therefore, the intelligent controller records the number of variances in one or more signal characteristics, and calculates the magnitude of each of the variances during a test of predefined duration. These may be displayed as normalized scores and averaged over several attempts on the part of the subject to complete the functional gait task. Further, the variances and scores may be stored in the system and used as a session by session measure of the subject's performance during motional training.

In visual feedback training and assessment, the subject 15*a* must use their VOR and postural control to complete the task. Repetition with various configuration (including those outlined hereinafter), greatly assist with VOR adaptation; especially when the task conditions are such that abnormal motion in the visual display provokes vestibular ocular symptoms. Therefore it is a specific objective to progressively change the conditions and dynamics associated with the task. For example, adaptation of the VOR can be complicated by moving the target in the opposite direction of the head movement, or providing drift to the target. This requires adaptation and compensation on the part of the subjects ocular gain for the eyes to stay on target. Other examples may include movements in different directions, for example the vertical plane as well as the horizontal plane. Once various speeds are accomplished, the exercises can be further maximized by performing them with a complex background as described in more detail hereinafter.

Figure 7A:
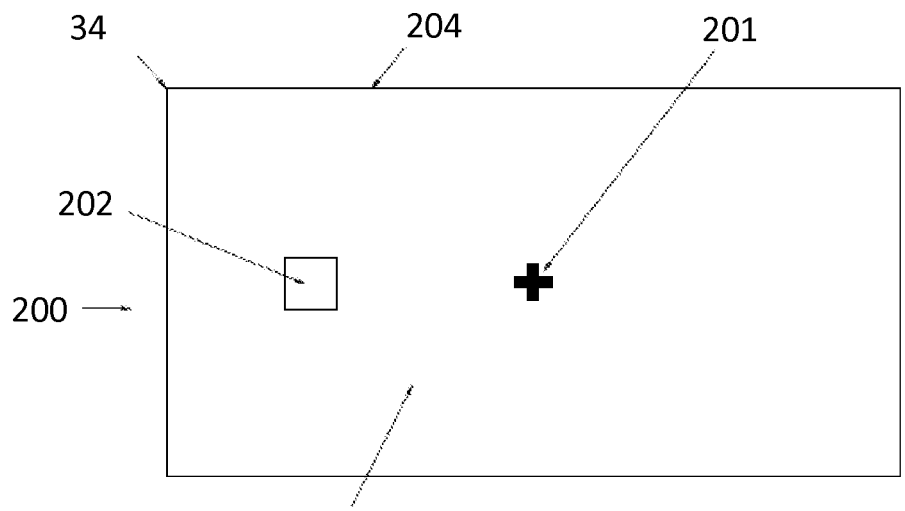
FIGS. 7A-7D illustrate particular aspects of a visual display according to aspects of the present invention.
Figure 7B:
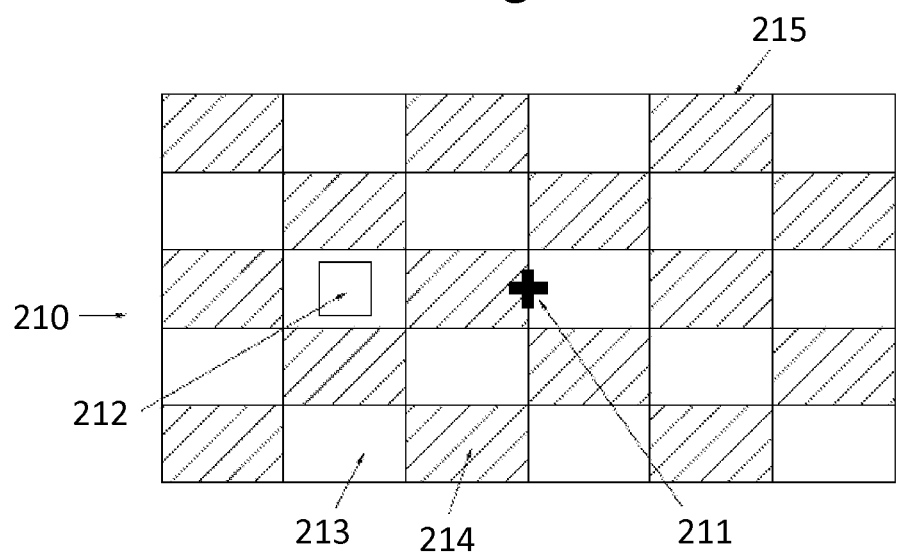

FIG. 7B shows a similar display view 210 to FIG. 7A, that may be shown during therapy or assessment. Two visual markers are provided, the first 211 is a visual marker on which the subject should attempt to fix their gaze during the visual motional training activity. In one embodiment, the second visual marker 212 may be a target that must be identified by the subject, and may appear at any random location on the display 215. During assessment, the time to respond and the number of correctly identified targets would be used as a basis for a functional visual acuity test.

In another visual feedback motional training and assessment embodiment, target 212 may be represented by an enclosed area (for example the interior of a box). The subject is required to move their head position to control the screen position of visual marker 211 such that visual marker 211 is located within (or captures) the target 212.

In this embodiment, the screen 215 background is designed to be a visual distraction pattern, comprised of alternately checkered blocks. Light 213 or dark 214 blocks are arranged as a background over the complete screen 215 area, while target 212 and visual marker 211 are superimposed on the background. The size of the blocks 213 and 214 may be altered by the therapist, system or user depending on the visual task and activity. Further the background pattern may move or in a predetermined manner at a rate that is set by the therapist, system or user.

In another embodiment of this invention, the background scrolls in response to the subjects head movements; a head worn inertial sensor provides the intelligent controller 20 with data regarding the head orientation which can be programmed to modulate the direction of the background. Therefore in this configuration the visual marker 211 and target 212 remain at the same location on the screen but the background pattern moves relative to these items.

Figure 7C:
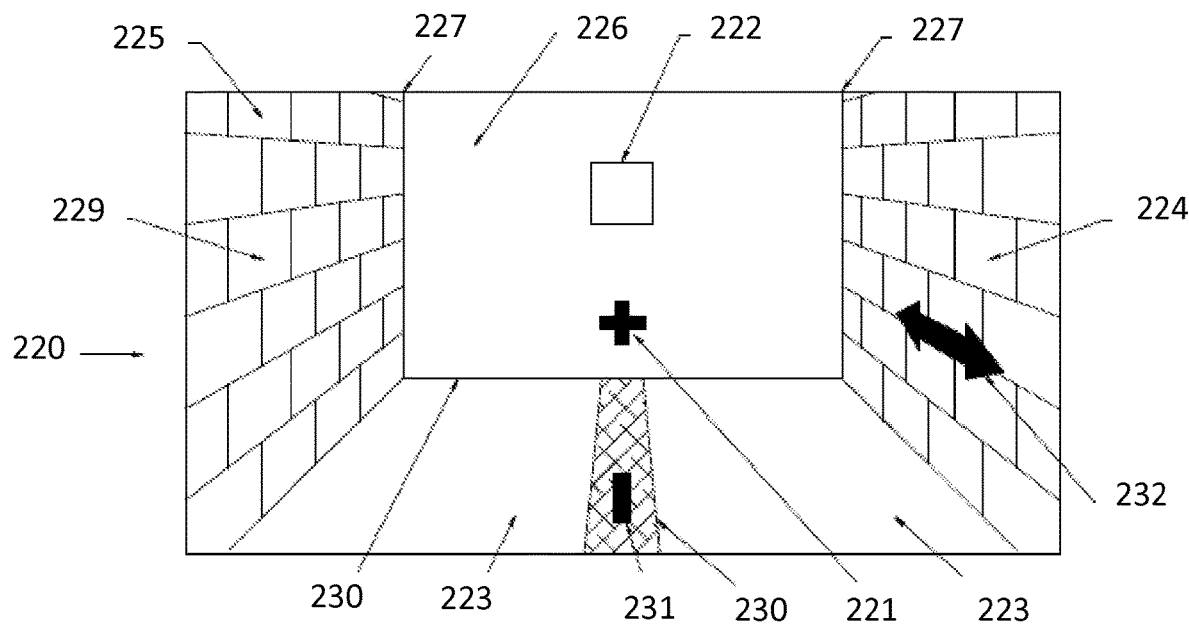

FIG. 7C shows another alternate display view 220 that may be shown during therapy or assessment. A three dimensional visual scene is provided and a visual motional activity task is presented. Two visual side walls 229 and 224 represent the left and right visual field boundaries, visual area 223 represents a floor region, and visual area 226 represents the far field view. Line transitions 227 and 230 are provided to complete the perspective view of the visual scene. Two visual objects may also be provided, the first is a visual marker 221 on which the subject should attempt to fix their gaze during the visual motional training activity. The second visual target 222 may be a transient target that must be identified by the subject, and may appear at any random location on the display 215. During assessment, the time to respond and the number of correctly identified targets would be used as a basis for a functional visual acuity test. An additional feature is the visual distraction pattern comprising checkered blocks or textures on the wall 229, 224 elements and floor 223.

In another visual feedback motional training and assessment preferred embodiment, target 222 may be represented by an enclosed area (for example the interior of a box). The subject is required to move their head position to control the screen position of visual marker 221 such that visual marker 221 is located within (or captures) the target 222. Visual side walls 229 and 224 may in certain embodiments be made up of aforementioned, light and dark distraction pattern elements. Further, the distraction patterns may be designed to move 231 and visually scroll, such to evoke the visual illusion of forward, or backward movement depending on the scroll direction. In further a preferred embodiment, visual display 220 may be simultaneous with a postural control task, where the subject 15a is required to maintain their COP or COG position 232 within predefined mediolateral boundaries 230. If the COP or COG position 232 moves outside said predefined boundaries into a region 223, a variance occurs and this may be used as an assessment parameter and as a multimodal sensory feedback parameter as described hereinbefore.

Figure 7D:
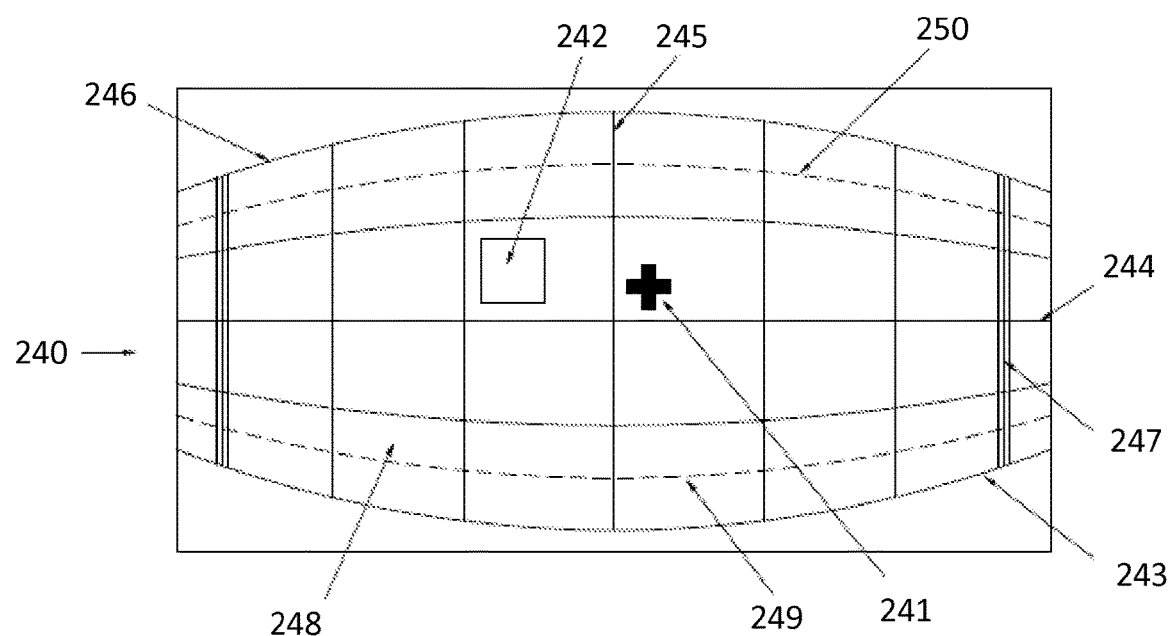

FIG. 7D shows another alternate display view 240 that may be shown during therapy or assessment. Two visual objects are provided, in one embodiment, the first 241 is a visual marker on which the subject should attempt to fix their gaze during the visual motional training activity. The second visual target 242 may be a target that must be identified by the subject, and may transiently appear at any random location on the active display 246. During assessment, the time to respond and the number of correctly identified targets would be used as a basis for a functional visual acuity test. An additional feature is the background visual distraction pattern comprising a visual scene of a section of a sphere with horizontal lines 244 and vertical lines 245. The size of the sphere and block surfaces 248 may be altered by the therapist or user depending on the visual activity. Further the pattern or texture on the sphere can be altered and may move or in a predetermined manner at a rate that is set by the therapist or user. In another embodiment of this invention, the background scrolls in response to the subjects head movements; a head worn inertial sensor provides the intelligent controller with data regarding the head orientation which can be programmed to modulate the direction of the background. Therefore in this configuration the visual marker 241 and target 242 remain at the same location on the screen but the background pattern moves relative to these items. In another embodiment of this invention, vertical limits such as 250 and 249 may be presented on the visual display. These limits are typically used as part of a protocol where the subject moves their head in pitch (up and down), the head position being measured by the head worn inertial sensor 46. Similarly, horizontal limits such as 246 and 247 can be provided in the display view and used in a related protocol with side to side head movements.

In another embodiment of this invention, the visual marker 241 is varied in response to the subjects head movements; a head worn inertial sensor 46 provides the intelligent controller with data regarding the head orientation which can be programmed to directly modulate the position of the visual marker. Therefore in this configuration, the visual marker will move during any head movements, which if not appropriately countered by visual saccades and other reflexes, will result in the apparent blurring of the visual target. The gain or modulation transfer function between the measured head movement and the target position on the visual screen is varied by the therapist, or in another embodiment, by the subject, using a computer interface 21 or remote interface 41. Preferably a test protocol is used to instruct the subject on the postural task (for example a sanding balance task on a compliant surface), together with a range of visual displays where the visual target appears with various gain settings and the subject is instructed to state whether the visual target is in focus for that particular presentation. In a more advanced test configuration, the visual target may be dynamic and the subject may have to report what on what they perceived; for example, various words may be presented or scrolled and the subject would have to recognize and repeat these (i.e. proving that they have correctly identified them). The gain or modulation is an indirect measurement of the dynamic visual ocular gain. The test can also be adaptable and change the gain based on the postural and visual task performance of the subject. Further, the screen background pattern can be also set to move relative to the target items acting as an additional source of visual distraction.

It is known that functional activities that involve unpredictable (passive) head perturbations (e.g. unexpectedly stepping off of a curb, vehicular travel, ambulation) can present significant gaze stabilization challenges to people with vestibular hypofunction and have been shown to reduce visual acuity. Therefore it is advantageous to conduct dynamic visual target assessment actives during dynamic movement tasks such as stepping, limited gait and postural tasks involving head movement.

Figure 8:
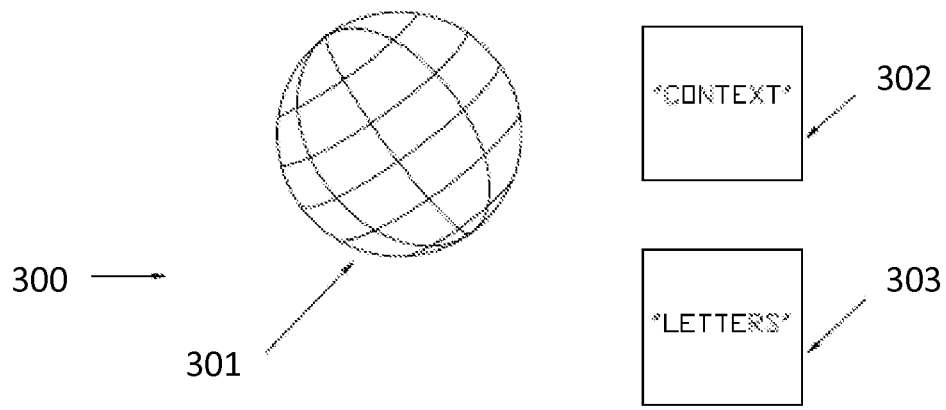
FIG. 8 illustrates specific examples of visual targets according to aspects of the present invention.

FIG. 8 shows specific examples 300 of complex visual targets for use in this invention. These visual targets can be computer generated three dimensional images 301, text based 302, 303, or brief animations. The visual targets should be designed to be recognizable and identifiable to the subject. The images 301 can, in some embodiments be implemented such that they rotate at various rates and orientations. Further the image size, color, contrast, textures and forms can be varied changing the visual salient features. In other examples, the text size, orientation, font, colors, contrast and nature can be varied changing the visual salient features.

Figure 9:
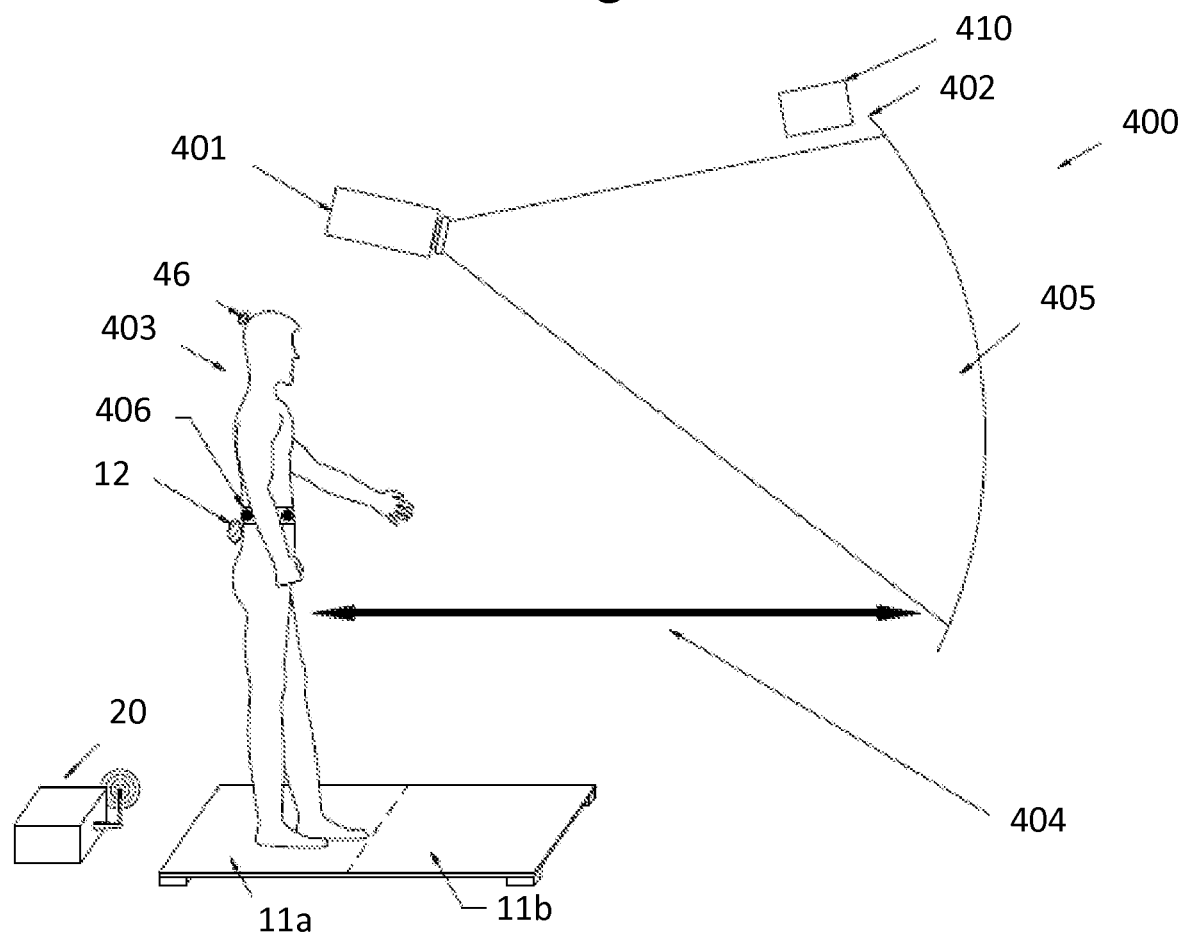
FIG. 9 illustrates another embodiment of a multimodal sensory feedback multimodal sensory feedback motional training system according to aspects of the present invention.

FIG. 9 shows another embodiment of the invention where the visual display 44 described previously is implemented using a projector 401 and large screen 402. This approach gives a wide field of view 405 to the subject 403; this is beneficial as visual distraction is most effective on large displays and self-motion and vection can be induced through movement in the visual scene or background layers. Similar visual display effects may also be obtained by using multiple screens and scaling the image across several adjacent screens. Specialist curved screens 402 may also be suitable for the reduction of visual distortion, especially in the peripheral field.

The subject 403 is also able to stand at a distance 404 from the visual display 405, therefore there is a relatively large area in which the subject may conduct dynamic motional training activities such as gait.

Changes in the direction and or rate of the background distraction layers are particularly effective as an unreliable visual input. Therefore visual displays such as those described in FIG. 1 and FIG. 8 may be used in this embodiment. As described hereinbefore, vibrotactile feedback 406 is provided with a torso worn actuators, auditory feedback may be provided with discrete or body worn actuators. Various sensor types and sensor combinations may be input to the intelligent controller 20; for example, one or more force plates 11*a* and 11*b*, inertial sensor 12 or 3D camera sensors 410 may be used. Sensors such as force plate sensors and a head worn inertial sensor 46 may be preferably used in combination during vestibular ocular motional training activities, or in other embodiments through torso worn inertial sensor 12 used in combination with the head worn inertial sensor 46.

Figure 10:
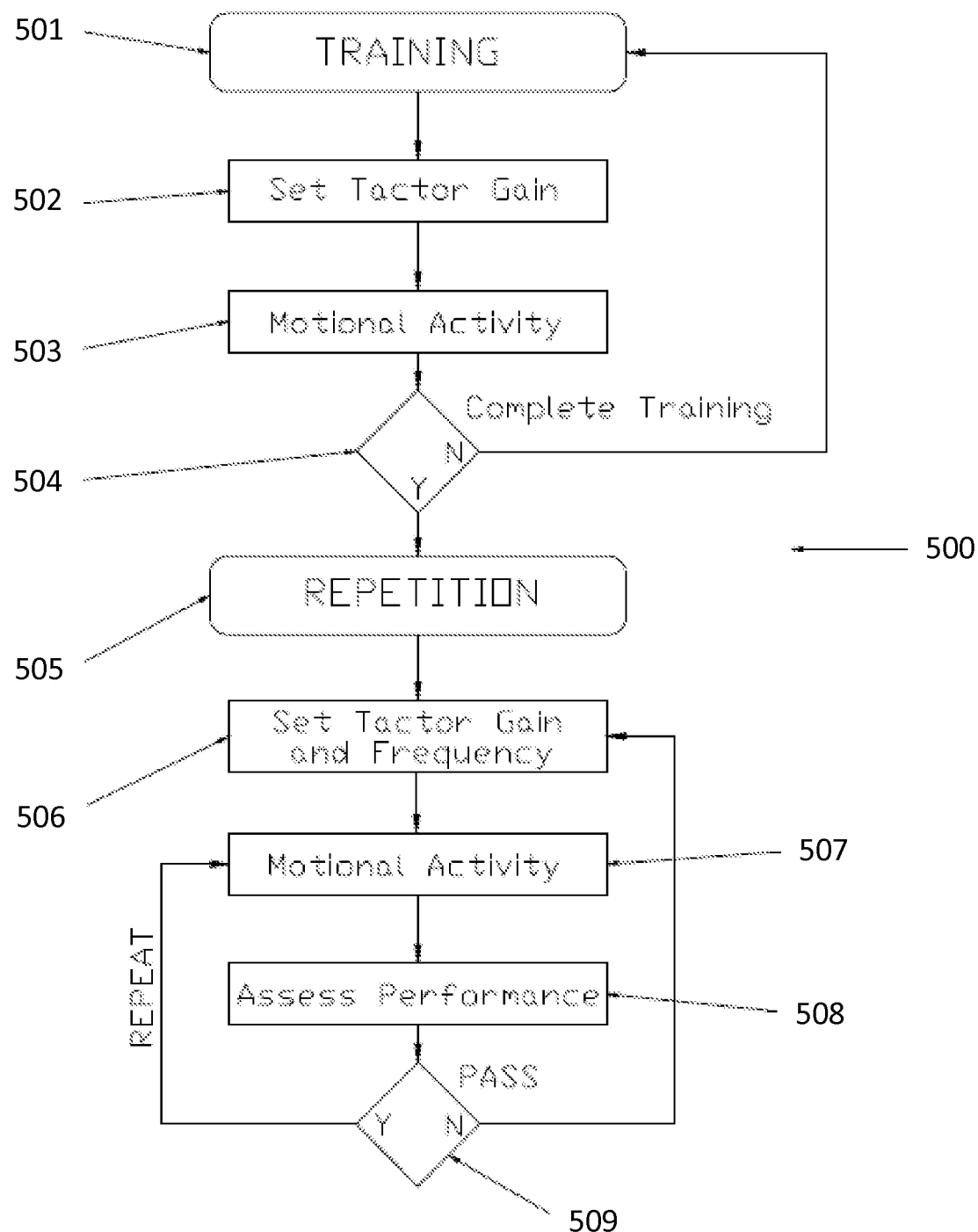
FIG. 10 illustrates a flow diagram according to aspects of the present invention.

FIG. 10 illustrates a flow diagram according to aspects of the present invention. The flow diagram 500 shows a means for providing vibrotactile feedback during therapy whereby the gain of the tactors is adjusted based on the stage of therapy and the performance of the subject assessed during motional therapy. During initial motional activity training 501, the vibrotactile feedback gain 502 would be set to a high level, for example 20 dB above the threshold for sensitivity (Re 1 micrometer). A particular motional activity 503 would then be illustrated and depending on the stage of the therapy 504, continued or progressed to a repetitive 505 training regimen. During the subsequent training and repetition 505 exercises, the vibrotactile parameters are adjusted 506. Typically the vibrotactile gain and displacement should be lowered (to about 1 to 10 dB above the threshold for sensitivity) and further, low frequency, between 60 to 120 Hz, tone burst vibration stimulation should preferably be used as the feedback stimuli. Motional activities are then performed 507 and concurrently assessed 508 using predetermined assessment features such as COP rms, diffusion coefficient and higher order parameter analysis such as variance, rate of variance. If the assessment shows the subject performing below predefined limits 509, the tactile gain is adjusted and increased. If the assessment shows the subject performing within acceptable predefined limits, the gain is unchanged or lowered from the previous value.

Figure 11:
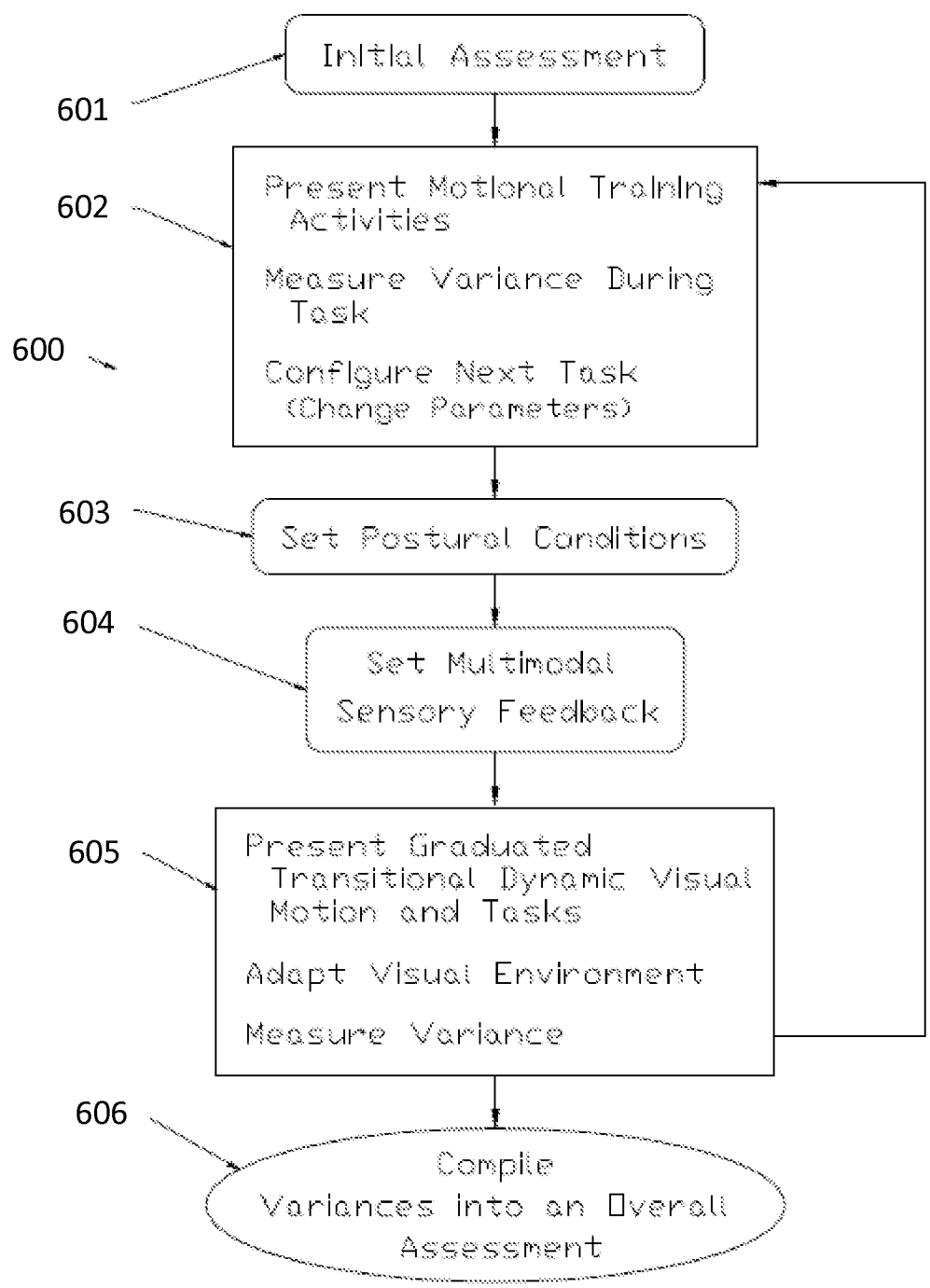
FIG. 11 further illustrates a flow diagram according to aspects of the present invention.

FIG. 11 illustrates a flow diagram according to further aspects of the invention. A vestibular ocular motional training exercise and assessment system has been described in the descriptions hereinbefore. It is known that subject's who repeat motional training task activities over the course of therapy usually report a progressive waning of symptoms of imbalance, disequilibrium, and motion-induced unsteadiness. This is due to compensation of a vestibular deficit where the remaining central nerve system processes allow sufficient control of eye, head, and body movements to maintain stable gaze, posture, and position. Therefore method 600 provides steps for providing graduated transitional motion and feedback configurations for vestibular ocular system recovery. This method involves several steps related to assessment, the results of which are used to determine subsequent visual feedback motional training configurations.

A vestibular exercise program typically includes exercises designed to improve ocular stability and balance. The initial assessment 601 measures postural and especially dynamic visual acuity using the systems described hereinbefore. The subject variance together with specific parameter scores such as test timing and accuracy is combined into a score and compared to previously stored data. Depending on this score, the therapist may decide at what level to begin multimodal sensory feedback motional training, and what specific vestibular ocular motional training activities are needed. These parameters then determine the initial motional activities 602 that may be administered with different postural conditions 603, such as with the subject seated, standing or completing functional movements. It is useful for the subject to complete and master, seated and simple visual acuity tasks (without head movement) prior to attempting more challenging postural configurations (such as standing) and adding head movements.

It is advantageous to further adapt and set the multimodal sensory feedback parameters 604; for example postural feedback should be optimally administered with vibrotactile components set to threshold limits where the subject is able to perform the balance task with variances occurring at greater than 1 second intervals. Thus, if the threshold is set too tight, the variance will occur at too high a rate for the feedback to be effective. Similarly, auditory feedback may be provided congruent with the vibrotactile cueing, or as separate parameter limit cueing (as described hereinbefore).

In each postural and feedback configuration, it is then preferable to complete various visual motional tasks 605. These tasks, described hereinbefore, should provoke the subjects vestibular ocular reflex, where the subject will have to repeat, and internally adapt and habituate to a multitude of visual and movement related conditions and configurations. As improvement occurs, head movements should be added while the subject is standing and walking; these head movements should be slow at first and later rapid and in all directions. Balance exercises such as walking with one foot placed directly in front of the other or walking on a narrow beam may also be then added.

Subject compliance and performance can be assessed 606 by determining the variance during specific visual and motional training activities.

In embodiments of this invention, it is useful for the subject to use a head mounted display (HIVID). HMD's are commercially available as virtual reality (VR) headset displays and also as augmented reality displays (AR). It is useful to compare features of VR and AR. AR provides a transparent viewscreen, so that the real scene has digital images and information superimposed on it (hence "augmented" reality). AR is therefore a combination of the real environment with programmable virtual features. VR occludes the real scene with one or more screens, but the real scene can potentially be displayed using a forward-facing camera. Both VR and AR have internal motion tracking sensors which may be, for example, inertial sensors, that may also include accurate headset position measurement. VR and AR can be used to create a complete three dimensional virtual world that can display one or more visual target objects, visual display objects or background objects as described hereinbefore.

Eye tracking sensors such as cameras can also be included within a VR or AR HIVID display and thus provide a measurement of the subject's eye gaze vector with respect to the headset. Combining the HIVID orientation and eye gaze vector allows the measurement of the subject's eye gaze vector within the virtual space. The eyes use vergence to focus on nearby visual objects, but for objects beyond the near field, about 45 inches from the eyes, the eyes diverge until they are parallel, but still effectively fixating at the same point. Thus, the eye gaze vector for objects that are not in the near field can be inferred from a single eye orientation measurement, or, for objects in the near field, eye gaze vector may be taken as an average of the eye gaze vector of each eye as determined by the measurement of each eye orientation.

Figure 12A:
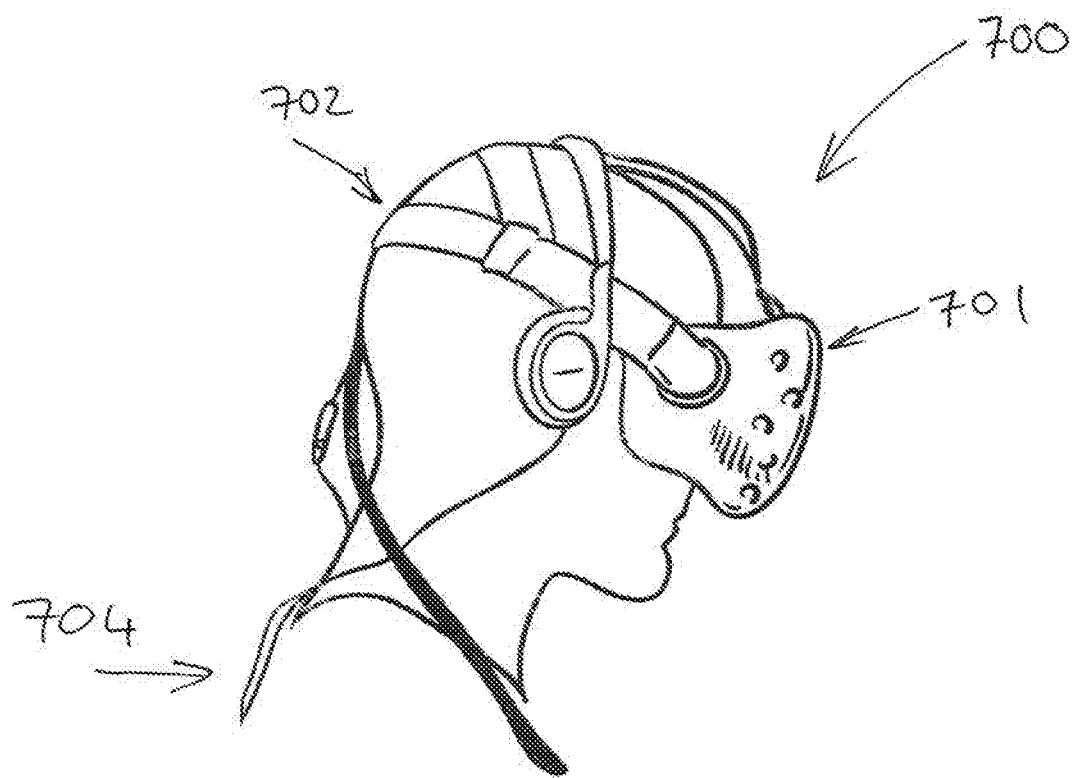
FIGS. 12a and 12b depict a head mounted display as may comprise embodiments of the system and method of the invention.
Figure 12B:
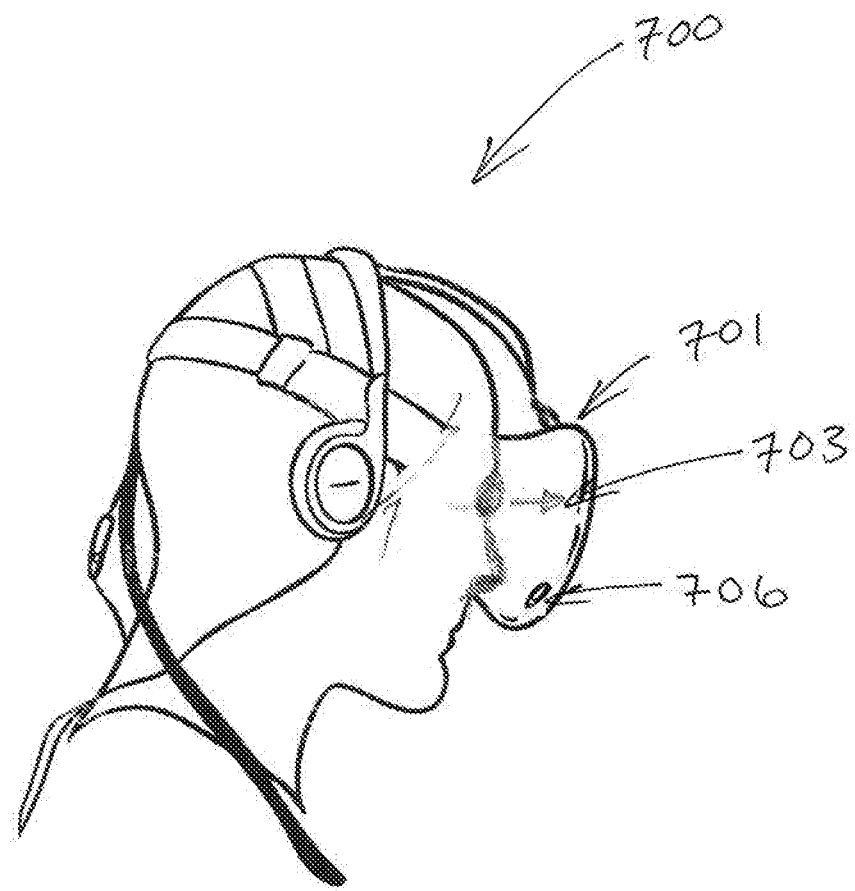

The HIVID 700 is shown in FIGS. 12*a* and 12*b*. A wearable HIVID AR or VR display containing visual screens, cameras or image projectors 701 is used to provide a virtual visual display to a subject 704. The HIVID can contain motion tracking sensors 702 and eye tracking sensors 706 that can be used to measure the subject 704's eye gaze vector 703.

As used herein, "memory", "medium", "media", "computer readable memory", "computer readable medium", "storage media", "computer readable storage media" and "computer readable storage medium" shall include within their meanings only physical non-transitory computer readable hardware, and such terms shall specifically exclude signals per se, carrier waves, propagating signals and other transitory signals. Such physical non transitory computer readable media may comprise hardware memory that comprises a physical structure for storing data which may include non-transitory computer executable instructions or data.

The electronic devices described herein may comprise a processor or other processing circuitry. As used herein, the term 'circuitry' or 'computer' refers to at least all of the following: hardware-only implementations (such as implementations in only analog and/or digital circuitry) and to combinations of circuits and software and/or firmware such as to a combination of processors or portions of processors/software including digital signal processor(s), software, and memory(ies) that work together to cause an apparatus, such as a mobile phone or tablet, to perform various functions and to circuits, such as a microprocessor(s) or portion of a microprocessor(s), that require software or firmware for operation, even if the software or firmware is not physically present. This definition of 'circuitry' applies to all uses of this term in this application, including in any claims. As a further example, as used in this application, the term "circuitry" would also cover an implementation of merely a processor, multiple processors, or portion of a processor and its (or their) accompanying software and/or firmware. As used herein, the terms "processor" and "controller" may be used interchangeably and have the same meaning—which is any system or device capable of reading and executing non-transitory computer-readable and computer-executable instructions.

The methods and systems of the invention may be implemented and carried out by circuitry or computers, e.g. processors or controllers, or any electronic device capable of executing non-transitory computer readable and executable instructions. Such circuitry may be in communication with computer readable memory comprising computer readable and executable instructions for carrying out the system and method of the invention.

Embodiments of the invention may be implemented in software, hardware, application logic or a combination of software, hardware, and application logic. The software application logic and/or hardware may reside on the apparatus, a separate device, or a plurality of separate devices. If desired, part of the software application logic and/or hardware may reside on the apparatus, part of the software, application logic and/or hardware may reside on a separate device, and part of the software, application logic and/or hardware may reside on a plurality of separate devices. In an example embodiment, the application logic, software, or an instruction set is maintained on any one of various conventional computer-readable media. In the context of this document, a "computer-readable medium" may be any tangible media or means that can contain, or store the instructions for use by or in connection with an instruction execution system, apparatus, or device, such as a computer. A computer readable medium may comprise a computer-readable storage medium that may be any tangible media or means that can contain or store the instructions for use by or in connection with an instruction execution system, apparatus, or device, such as a computer.

While various embodiments in accordance with the present invention have been shown and described, it is understood that the invention is not limited thereto. The present invention may be changed, modified and further applied by those skilled in the art. Therefore, this invention is not limited to the detail shown and described previously, but also includes all such changes and modifications.

We claim:

1. A method for the assessment and treatment of disequilibrium, balance and motion disorders, comprising:
    displaying a moving visual target on a visual display said target comprising a pre-defined area having one or more target limit parameters;
    presenting said visual display to a subject within a field of vision of said subject;
    identifying a location on a visual display at which said subject is to direct their gaze by moving their head;
    controlling said visual target's size and location on said visual display by at least one processor which is in electrical communication with said visual display; and
    measuring said subject's head position and orientation using a head gaze sensor; and
    wherein said head gaze sensor provides a signal representing a measure of said subject's head gaze vector while the subject attempts to move their head to direct their gaze at said visual target; and
    wherein at least one processor is in electrical communication with said head gaze sensor, and wherein said at least one processor is capable of placing a visual marker on said display which represents said subject's head gaze vector; and
    wherein said visual marker is represented by a marker signal; and
    wherein said visual target and said visual marker provide visual feedback to the subject of their ability to direct their head gaze at said target;
    wherein said at least one processor calculates the magnitude of a first variance in position as a measurement of distance between said visual marker and said visual target, said first variance in position occurring when said marker signal exceeds said one or more target limit parameters;
    wherein said visual feedback assists the subject to reduce said first variance in position between said visual marker and said visual target; and
    wherein said magnitude of said first variance in position provides a measure of the subject's ability to direct their gaze at said target in an attempt to place said visual marker within said one or more target limit parameters.

2. The method of claim 1, wherein a visual background distraction is displayed on said visual display, wherein said visual background distraction is selected from the group consisting of a static visual image and a moving visual image.

3. The method of claim 2, further comprising the step of scaling the visual background distraction.

4. The method of claim 3, wherein said visual display is further defined as being a part of a virtual reality or augmented reality headset worn by said subject.

5. The method of claim 3, wherein said head gaze sensor is further defined as being a part of a virtual reality or augmented reality headset worn by said subject.

6. The method of claim 2 in which the movement of said moving visual target is defined as being variable in rate and extent by said at least one processor.

7. The method of claim 2, wherein said visual display is further defined as being a part of a virtual reality or augmented reality headset worn by said subject.

8. The method of claim 2, wherein said head gaze sensor is further defined as being a part of a virtual reality or augmented reality headset worn by said subject.

9. The method of claim 1 in which the movement of said moving visual target is defined as being variable in rate and extent by said at least one processor.

10. The method of claim 1 further comprising the step of measuring a biomechanical state of said subject using a postural sensor selected from the group consisting of a force plate, an inertial sensor and a 3D camera, wherein said postural sensor is in electrical communication with said at least one processor, and wherein said at least one processor is capable of measuring a second variance between at least one biomechanical state predetermined parameter and said biomechanical state of said subject while said subject performs at least one predetermined task.

11. The method of claim 10, further comprising the step of combining said second variance between said visual marker and said visual target and said second variance between said at least one biomechanical state predetermined parameter and said biomechanical state of said subject while said subject performs at least one predetermined task to produce an assessment of said subject's performance.

12. The method of claim 10, wherein said visual display is further defined as being a part of a virtual reality or augmented reality headset worn by said subject.

13. The method of claim 10, wherein said head gaze sensor is further defined as being a part of a virtual reality or augmented reality headset worn by said subject.

14. The method of claim 1, further comprising the step of providing additional feedback to said subject, said feedback selected from the group consisting of vibrotactile feedback and auditory feedback.

15. The method of claim 14, wherein said head gaze sensor is further defined as being a part of a virtual reality or augmented reality headset worn by said subject.

16. The method of claim 1, wherein said visual display is further defined as being a part of a virtual reality or augmented reality headset worn by said subject.

17. The method of claim 1, wherein said head gaze sensor is further defined as being a part of a virtual reality or augmented reality headset worn by said subject.

* * * * *